United States Patent
Tseng et al.

(10) Patent No.: US 10,823,736 B2
(45) Date of Patent: Nov. 3, 2020

(54) METHOD OF ASSESSING DISEASE CONDITION OF CANCER

(71) Applicants: The Regents of the University of California, Oakland, CA (US); Cedars-Sinai Medical Center, Los Angeles, CA (US)

(72) Inventors: Hsian-Rong Tseng, Los Angeles, CA (US); Jiaoti Huang, Los Angeles, CA (US); Edwin M. Posadas, Los Angeles, CA (US); Jiefu Chen, Los Angeles, CA (US); Hao Ho, Los Angeles, CA (US); Zunfu Ke, Los Angeles, CA (US); Ker-Chau Li, Los Angeles, CA (US); Yi-Tsung Lu, Los Angeles, CA (US); Jake Lichterman, Los Angeles, CA (US); Min Song, Los Angeles, CA (US); Leland W. K. Chung, Los Angeles, CA (US)

(73) Assignees: The Regents of the University of California, Oakland, CA (US); Cedars-Sinai Medical Center, Los Angeles, CA (US)

( * ) Notice: Subject to any disclaimer, the term of this patent is extended or adjusted under 35 U.S.C. 154(b) by 298 days.

(21) Appl. No.: 15/514,438

(22) PCT Filed: Sep. 28, 2015

(86) PCT No.: PCT/US2015/052736
§ 371 (c)(1),
(2) Date: Mar. 24, 2017

(87) PCT Pub. No.: WO2016/049658
PCT Pub. Date: Mar. 31, 2016

(65) Prior Publication Data
US 2017/0299595 A1    Oct. 19, 2017

Related U.S. Application Data

(60) Provisional application No. 62/056,321, filed on Sep. 26, 2014.

(51) Int. Cl.
    *G01N 33/574*    (2006.01)
    *G01N 15/14*    (2006.01)
    (Continued)

(52) U.S. Cl.
    CPC ....... *G01N 33/57434* (2013.01); *G01N 15/10* (2013.01); *G01N 15/1475* (2013.01);
    (Continued)

(58) Field of Classification Search
    None
    See application file for complete search history.

(56) References Cited

U.S. PATENT DOCUMENTS

2012/0003711 A1    1/2012  Tseng et al.
2012/0276555 A1*  11/2012  Kuhn ................. G01N 33/5076
                                                   435/7.23

(Continued)

FOREIGN PATENT DOCUMENTS

WO    WO-2014-008155 A1    1/2014

OTHER PUBLICATIONS

Lu et al., NanoVelcro Chip for CTC enumeration in prostate cancer patients, Methods, (64), pp. 144-152, available online Jun. 29, 2013. (Year: 2013).*

(Continued)

*Primary Examiner* — Rebecca M Giere
(74) *Attorney, Agent, or Firm* — Venable LLP; Henry J. Daley; Miguel A. Lopez

(57) ABSTRACT

A method, system and computer-readable medium for assessing a disease condition of a cancer of a subject, including: receiving a blood sample from the subject; iso- (Continued)

lating a plurality of circulating tumor cells (CTCs) from the blood sample; measuring at least one of cell or cell nucleus sizes of each of the plurality of CTCs; determining a measured CTC size distribution of the plurality of CTCs based on the measuring; comparing the measured CTC size distribution to a reference CTC size distribution using a computer; and assigning the disease condition of the cancer of the subject based on the comparing.

23 Claims, 20 Drawing Sheets

(51) Int. Cl.
G01N 33/569 (2006.01)
G01N 15/10 (2006.01)

(52) U.S. Cl.
CPC . *G01N 33/56966* (2013.01); *G01N 33/57488* (2013.01); *G01N 2015/1006* (2013.01); *G01N 2015/1488* (2013.01); *G01N 2015/1493* (2013.01); *G01N 2015/1497* (2013.01); *G01N 2800/56* (2013.01)

(56) References Cited

U.S. PATENT DOCUMENTS

2012/0315690 A1* 12/2012 Di Carlo ............... G01N 15/10
 435/287.1
2013/0171642 A1 7/2013 Pestano et al.

OTHER PUBLICATIONS

Aceto et al., "Circulating tumor cell clusters are oligoclonal precursors of breast cancer metastasis," Cell, Aug. 2014, vol. 158, No. 5, pp. 1110-1122.
Chen et al., "Subclassification of prostate cancer circulating tumor cells by nuclear size reveals very small nuclear circulating tumor cells in patients with visceral metastases," Cancer, Sep. 15, 2015, vol. 121, No. 18, pp. 3240-3251.
International Search Report and Written Opinion in International Application No. PCT/US2015/052736, dated Dec. 28, 2015.
Office Action in corresponding Chinese Patent Application No. 201580064526.9, dated Mar. 21, 2019 (with English language translation).
Zhao L, et al., "High-Purity Prostate Circulating Tumor Cell Isolation by a Polymer Nanofiber-Embedded Microchip for Whole Exome Sequencing" Adv Mater. pp. 2897-2902 (2013).
Aceto et al., "Circulating tumor cell clusters are oligoclonal precursors of breast cancer metastasis," Cell, August, vol. 158, No. 5, pp. 1110-1122 (2014).
Akaike H., "A new look at the statistical model identification", IEEE Transactions Automatic Control. 19:716-72 (1974).
Akfirat et al., "Tumour cell survival mechanisms in lethal metastatic prostate cancer differ between bone and soft tissue metastases", J Pathol. 230:291-297 (2013).
Alix-Panabieres et al., "Challenges in circulating tumour cell research" Nat Rev Cancer, 14: 623-631 (2014).
Amato et al., "Epithelial cell adhesion molecule-positive circulating tumor cells as predictive biomarker in patients with prostate cancer", Urology 2013;81(6):1303-7.
Aparicio, et al. "Platinum-based chemotherapy for variant castrate resistant prostate cancer", Clin Cancer Res 2013;19 (13):3621-30.
Attard et al., "Selective inhibition of CYP17 with abiraterone acetate is highly active in the treatment of castration-resistant prostate cancer", J Clin Oncol. 27: 3742-3748 (2009).
Baak JP. "The principles and advances of quantitative pathology", Anal Quant Cytol Histol 1987;(2):89-95.
Baccelli et al., "Identification of a population of blood circulating tumor cells from breast cancer patients that initiates metastasis in a xenograft assay", Nat Biotechnol. 31:539-544 (2013).
Beltran et al., "Challenges in recognizing treatment-related neuroendocrine prostate cancer", J Clin Oncol. 30(36); e386-389 (2012).
Beltran et al., "Aggressive Variants of Castration-Resistant Prostate Cancer", Clin Cancer Res, 20(11):2846-50 (2014).
Bobek et al., "Site-specific cytomorphology of disseminated PC-3 prostate cancer cells visualized in vivo with fluorescent proteins", Diagn Cytopathol. 41: 413-417 (2013).
Broström G. Generalized linear models with clustering 2009. Available from URL: http://cran.r-project.org/web/ packages/glmmML/glmmML.pdf.
Chan et al., "Advanced technologies for studying circulating tumor cells at the protein level", Expert Rev Proteomics. 10:579-589 (2013).
Coumans et al., "All circulating EpCAM+CK+CD45- objects predict overall survival in castration-resistant prostate cancer", Ann Oncol 2010;21(9):1851-7.
Coumans et al., "Filter characteristics influencing circulating tumor cell enrichment from whole blood", PLoS One 2013;8(4):e61770.
Danila et al. "Circulating tumor cells as biomarkers in prostate cancer", Clin Cancer Res. 17(12): 3903-3912 (2011).
Danila et al., "Phase II multicenter study of abiraterone acetate plus prednisone therapy in patients with docetaxel-treated castration-resistant prostate cancer", J Clin Oncol. 28:1496-1501 (2010).
de Bono et al., "Circulating tumor cells predict survival benefit from treatment in metastatic castration-resistant prostate cancer", Clin Cancer Res. 14(19): 6302-6309 (2008).
Dempster et al., "Maximun Likelihood from Incomplete Data via the EM Algorithm" Journal of the Royal Statistical Society, Series B. 39:1-38 (1977).
Folkersma et al., "Prognostic significance of circulating tumor cell count in patients with metastatic hormone-sensitive prostate cancer" Urology. 80(6):1328-1332 (2012).
Folkersma et al., "Immunomagnetic quantification of circulationg tumoral cells in patients with prostate cancer: clincal and pathological correlation", Arch Esp Urol, (2010) vol. 63, No. 1, pp. 23-31.
Gandaglia et al., "Impact of the Site of Metastases on Survival in Patients with Metastatic Prostate Cancer", Eur Urol. (2014).
Goldkorn et al., "Circulating tumor cell counts are prognostic of overall survival in SWOG S0421: a phase III trial of docetaxel with or without atrasentan for metastatic castration-resistant prostate cancer", J Clin Oncol. 32 (11):1136-1142 (2014).
Goodman et al., "Circulating tumor cells as a predictive biomarker in patients with hormone-sensitive prostate cancer", Clin Genitourin Cancer 2011;9(1):31-8.
Haber et al., "Blood-based analyses of cancer: circulating tumor cells and circulating tumor DNA", Cancer Discov;4 (6):650-61 (2014).
Halabi et al., "The site of visceral metastases (mets) to predict overall survival (OS) in castration-resistant prostate cancer (CRPC) patients (pts): A meta-analysis of five phase III trials", J Clin Oncol. 32:5s,(suppl; abstr 5002) (2014).
Hou et al., "Clinical significance and molecular characteristics of circulating tumor cells and circulating tumor microemboli in patients with small-cell lung cancer", J Clin Oncol. 30: 525-532 (2012).
Hou et al., "Polymer nanofiber-embedded microchips for detection, isolation, and molecular analysis of single circulating melanoma cells", Angew Chem Int Ed Engl. 52: 3379-3383 (2013).
Kalykaki et al. "Elimination of EGFR-expressing circulating tumor cells in patients with metastatic breast cancer treated with gefitinib", Cancer Chemother Pharmacol 2014;73(4):685-93.
Kayser et al., "Quantitative pathology in virtual microscopy: history, applications, perspectives", Acta Histochem 2013;115(6):527-32.
Khan et al., "Quantitative alterations in nuclear structure predict prostate carcinoma distant metastasis and death in men with biochemical recurrence after radical prostatectomy" Cancer. 98(12): 2583-2591 (2003).

(56) References Cited

OTHER PUBLICATIONS

Klingauf et al., "Enhancement of U4/U6 small nuclear ribonucleoprotein particle association in Cajal bodies predicted by mathematical modeling", Mol Biol Cell., 17:4972-4981 (2006).

Kothari et al., "Pathology imaging informatics for quantitative analysis of whole-slide images", J Am Med Inform Assoc 2013;20(6):1099-108.

Krebs et al., "Molecular analysis of circulating tumour cells-biology and biomarkers", Nat Rev Clin Oncol. 11:129-144 (2014).

Leman et al., "Nuclear structure as a source of cancer specific biomarkers", J Cell Biochem 2008;104(6):1988-93.

Ligthart et al., "Circulating Tumor Cells Count and Morphological Features in Breast, Colorectal and Prostate Cancer", PLoS One. 8: e67148 (2013).

Lin et al., "Nanostructure embedded microchips for detection, isolation, and characterization of circulating tumor cells", Acc Chem Res. 47: 2941-2950 (2014).

Liotta et al., "The significance of hematogenous tumor cell clumps in the metastatic process" Cancer Res. 36: 889-894 (1976).

Lipianskaya et al. "Androgen-deprivation therapy-induced aggressive prostate cancer with neuroendocrine differentiation", Asian J Androl 2014; 10.4103/1008-682X.123669.

Lohr JG, et al., "Whole-exome sequencing of circulating tumor cells provides a window into metastatic prostate cancer", Nat Biotechnol. 32:479-484 (2014).

Lu et al., "NanoVelcro Chip for CTC enumeration in prostate cancer patients", Methods 64: 144-152 (2013).

Marrinucci et al., "Case study of the morphologic variation of circulating tumor cells", Hum Pathol. 38: 514-519 (2007).

Mohler et al., "Nuclear shape analysis for the assessment of local invasion and metastases in clinically localized prostate carcinoma", Cancer. 74(11): 2996-3001 (1994).

Moreno et al., "Circulating tumor cells predict survival in patients with metastatic prostate cancer", Urology. 65(4): 713-718 (2005).

Olmos et al., "Circulating tumour cell (CTC) counts as intermediate end points in castration-resistant prostate cancer (CRPC): a single-centre experience", Ann Oncol. 20(1): 27-33 (2009).

Pantel et al., "The potential of circulating tumor cells as a liquid biopsy to guide therapy in prostate cancer", Cancer Discov 2012;2(11):974-5.

Papandreou et al., "Results of a phase II study with doxorubicin, etoposide, and cisplatin in patients with fully characterized small-cell carcinoma of the prostate", J Clin Oncol 2002;20(14):3072-80.

Partin et al., "Use of nuclear morphometry, gleason histologic scoring, clinical stage, and age to predict disease-free survival among patients with prostate cancer", Cancer. 70: 161-168 (1992).

Pezaro et al., "Visceral disease in castration-resistant prostate cancer", Eur Urol. 65: 270-273 (2014).

Pond et al., "The prognostic importance of metastatic site in men with metastatic castration-resistant prostate cancer", Eur Urol. 65: 3-6 (2014).

Posadas et al., "A translational phase 2 study of cabozantinib in men with metastatic castration resistant prostate cancer with visceral metastases with characterization of circulating tumor cells and large oncosomes", Annals of Oncology. 25 (suppl_4): iv546-iv563 (2014).

Reid et al., "Significant and sustained antitumor activity in post-docetaxel, castration-resistant prostate cancer with the CYP17 inhibitor abiraterone acetate", J Clin Oncol. 28:1489-1495 (2010).

Ritchie et al., "Methods of integrating data to uncover genotype-phenotype interactions", Nat Rev Genet. 16: 85-97 (2015).

Roodman GD., "Mechanisms of bone metastasis", N. Engl J Med 2004;350(16):1655-64.

Scatena et al., "Circulating tumour cells and cancer stem cells: a role for proteomics in defining the interrelationships between function, phenotype and differentiation with potential clinical applications", Biochim Biophys Acta. 1835: 129-143 (2013).

Scher et al., "Circulating tumour cells as prognostic markers in progressive, castration-resistant prostate cancer: a reanalysis of IMMC38 trial data", Lancet Oncol. 10(3): 233-239 (2009).

Schwarz, GE., "Estimating the dimension of a model", Annals of Statistics. 6: 461-464 (1978).

Siegel et al., "Cancer statistics", CA Cancer J Clin. 64: 9-29 (2014).

Sweeney et al., "Impact on overall survival (OS) with chemohormonal therapy versus hormonal therapy for hormone-sensitive newly metastatic prostate cancer (mPrCa): An ECOG-led phase III randomized trial", J Clin Oncol. 5s, (suppl; abstr LBA2012) (2014).

Thalgott et al., "Detection of circulating tumor cells in different stages of prostate cancer", J Cancer Res Clin Oncol. 139(5): 755-763 (2013).

Veltri et al., "Nuclear morphometry, nucleomics and prostate cancer progression", Asian J Androl 2012;14(3):375-84.

Vesalainen et al.,"Nuclear morphometry is of independent prognostic value only in T1 prostatic adenocarcinomas", Prostate. 27:110-117 (1995).

Vinjamoori et al. "Atypical metastases from prostate cancer: 10-year experience at a single institution. AJR Am J Roentgenol" 199: 367-372 (2012).

Wang et al., "A higher number of circulating tumor cells (CTC) in peripheral blood indicates poor prognosis in prostate cancer patients—a meta-analysis", Asian Pac J Cancer Prev. 12(10): 2629-2635 (2011).

Wang et al., "Highly efficient capture of circulating tumor cells by using nanostructured silicon substrates with integrated chaotic micromixers", Angew Chem Int Ed Engl. 50(13):3084-3088 (2011).

Wicha et al., "Circulating tumor cells: not all detected cells are bad and not all bad cells are detected", J Clin Oncol. 29:1508-1511 (2011).

Yu et al., "Cancer therapy. Ex vivo culture of circulating breast tumor cells for individualized testing of drug susceptibility", Science. 345:216-220 (2014).

Yu et al., "Circulating breast tumor cells exhibit dynamic changes in epithelial and mesenchymal composition", Science. 339: 580-584 (2013).

Yuan et al., "Androgen receptor functions in castration-resistant prostate cancer and mechanisms of resistance to new agents targeting the androgen axis", Oncogene 2014;33(22):2815-25.

Zhao et al., "High-Purity Prostate Circulating Tumor Cell Isolation by a Polymer Nanofiber-Embedded Microchip for Whole Exome Sequencing", Adv Mater. pages 2897-2902 (2013).

Zink et al., "Nuclear structure in cancer cells", Nat Rev Cancer. 4(9): 677-687 (2004).

\* cited by examiner

METHOD OF ASSESSING DISEASE CONDITION OF CANCER

CROSS-REFERENCE OF RELATED APPLICATION

This application is a U.S. National Phase Application of PCT/US2015/052736, filed Sep. 28, 2015, which claims priority to U.S. Provisional Application No. 62/056,321 filed Sep. 26, 2014, the entire contents of which are hereby incorporated by reference.

This invention was made with Government support under Grant Nos. CA151159, 1CA157396, and CA092131 awarded by the National Institutes (NIH) of Health and Grant No. W81XWH-11-1-0422 awarded by the U.S. Army, Medical Research and Material Command. The Government has certain rights in the invention.

BACKGROUND

1. Technical Field

The field of the currently claimed embodiments of this invention relate to methods and systems for assessing a disease condition of a cancer of a subject, and more particularly to assessing a disease condition of a cancer of a subject using isolated circulating tumor cells from the subject.

2. Discussion of Related Art

Prostate cancer (PC) is the most common cancer affecting men in the United States. It is estimated that over 200,000 American men will be diagnosed with PC and close to 30,000 are expected to die of this disease in 2014 [1]. The 5-year survival rate of PC declines from nearly 100% for those diagnosed with localized disease (stage I) to 28% for those who present with metastatic disease (stage IV) [1]. It is widely recognized that PC is an osteotropic disease [2]. A subset of patients, however, develops metastases to visceral organs (e.g. liver or lungs). The appearance of visceral metastases correlates with significantly increased mortality [3]. This form of clinical progression often predicts imminent end organ failure leading to death. Visceral metastases are found in particularly aggressive subtypes of PC [4] which are not yet well-defined but include those carcinomas with neuroendocrine features or small cell carcinoma of the prostate. In such settings, non-androgen receptor targeted therapeutic strategies, including platinum-based chemotherapy [5, 6], have been suggested for these aggressive variants as they often possess resistance to conventional hormone therapy [7-9]. As such, there remains an overwhelming and unmet need to identify these aggressive PCs which will develop metastases to the visceral organs. Identification of these patients at earlier time points may allow for the administration of more appropriate treatment at a time when the natural history may be significantly altered. The same approach could potentially be used as part of clinical monitoring to measure the efficacy of therapies particularly beneficial to these subtypes.

There are no current PC biomarkers that can specifically predict the onset or presence of visceral metastasis. On the other hand, circulating tumor cells (CTCs) are recognized as an informative biomarker [10] for advanced disease with prognostic significance in multiple trials [11-18]. Moreover, we along with other groups have proposed that they may be used as a "liquid biopsy" [19]. Using conventional, FDA-approved approaches, CTC counts have not shown value in the detection of occult visceral spread [14]. It is suggested that additional information such as morphological analysis may be incorporated into CTC assay to improve the clinical value.

As one of the most commonly analyzed morphological features, nuclear shape in tumor sections has been correlated with distant metastasis and death in PC [20, 21]. Studies also revealed the alteration of numerous signaling pathways affecting nuclear structures at the scenario of malignancy [22]. It is thus conceivable that the nuclear morphology of CTCs may exhibit correlation with their capacity to form metastasis, and that nuclear shape analysis in conjunction with CTC-based assay via technical advances [23] that allow for a more sensitive and specific detection and isolation, could be used to detect more aggressive forms of disease such as those associated with visceral metastasis. Some embodiments of the present invention include methods, systems and computer readable mediums for assessing a disease condition of a cancer of a subject by analyzing the morphological features of isolated circulating tumor cells.

SUMMARY

A method of assessing a disease condition of a cancer of a subject, including: receiving a blood sample from the subject; isolating a plurality of circulating tumor cells (CTCs) from the blood sample; measuring at least one of cell or cell nucleus sizes of each of the plurality of CTCs; determining a measured CTC size distribution of the plurality of CTCs based on the measuring; comparing the measured CTC size distribution to a reference CTC size distribution using a computer; and assigning the disease condition of the cancer of the subject based on the comparing.

A method of assigning a metastatic stage of prostate cancer, including: receiving a blood sample from a subject with prostate cancer; isolating a plurality of circulating tumor cells (CTCs) from the blood sample using a device that has a nanostructured surface that enhances capture of CTCs preferentially over other types of cells and uses a combination of a microfluidic chaotic mixer and the nanostructured surface; measuring at least one of cell or cell nucleus sizes of each of the plurality of CTCs; determining a measured CTC size distribution of the plurality of CTCs based on the measuring; comparing the measured CTC size distribution to a reference CTC size distribution using a computer; and assigning a metastatic stage of the prostate cancer of the subject based on the comparing.

A system for assessing a disease condition of a cancer of a subject, including: a circulating-tumor-cell (CTC) isolation device; and a computer, the computer comprising a computer-readable medium comprising non-transient computer-executable code for assessing a disease condition of the cancer of the subject, the non-transient computer-executable code, when executed by the computer, causes the computer to perform steps including: receive measurements of at least one of cell sizes or cell nucleus sizes for each of a plurality of circulating tumor cells (CTCs) isolated from a blood sample from the subject; determine a measured CTC size distribution of the plurality of CTCs based on the measurements received; compare the measured CTC size distribution to a reference CTC size distribution; and assign the disease condition of the cancer of the subject based on the comparing.

A computer-readable medium including non-transient computer-executable code for assessing a disease condition of a cancer of a subject, the non-transient computer-executable code, when executed by a computer, causes the computer to perform steps including: receive measurements of at least one of cell sizes or cell nucleus sizes for each of a plurality of circulating tumor cells (CTCs) isolated from a blood sample from the subject; determine a measured CTC size distribution of the plurality of CTCs based on the measurements received; compare the measured CTC size distribution to a reference CTC size distribution; and assign the disease condition of the cancer of the subject based on the comparing.

BRIEF DESCRIPTION OF THE DRAWINGS

Further objectives and advantages will become apparent from a consideration of the description, drawings, and examples.

DETAILED DESCRIPTION

Figure 1A:
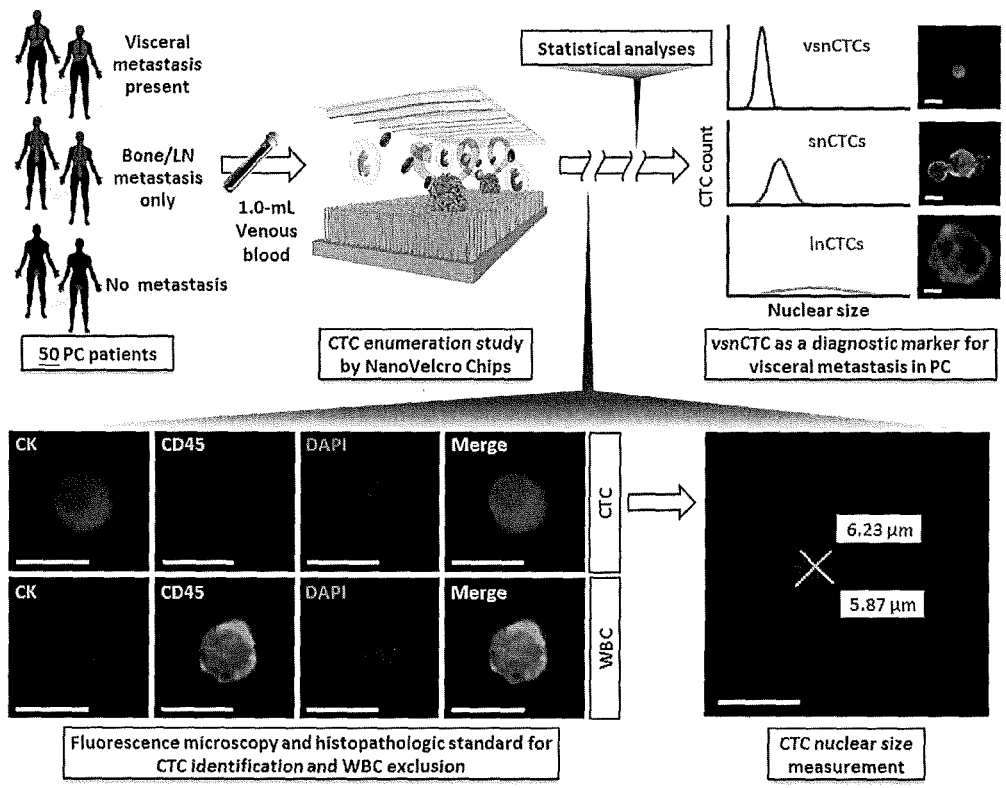
FIG. 1A shows a schematic of the study design.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the present invention are directed to methods of assessing a disease condition of a cancer of a subject including the steps of: receiving a blood sample from the subject; isolating a plurality of circulating tumor cells (CTCs) from the blood sample; measuring at least one of cell or cell nucleus sizes of each of the plurality of CTCs; determining a measured CTC size distribution of the plurality of CTCs based on the measuring; comparing the measured CTC size distribution to a reference CTC size distribution using a computer; and assigning the disease condition of the cancer of the subject based on the comparing. In some embodiments, the reference distribution is an empirically obtained size distribution that is resolved into a plurality of size-cluster distributions. In some embodiments, the plurality of size-cluster distributions is three different size-cluster distributions corresponding to large-nuclear CTCs, small-nuclear CTCs and very-small-nuclear CTCs, respectively.

Some embodiments of the present invention include systems for assessing a disease condition of a cancer of a subject. Such systems include: a circulating-tumor-cell (CTC) isolation device; and a computer, the computer comprising a computer-readable medium comprising non-transient computer-executable code for assessing a disease condition of the cancer of the subject, the non-transient computer-executable code, when executed by the computer, causes the computer to perform steps comprising: receive measurements of at least one of cell sizes or cell nucleus sizes for each of a plurality of circulating tumor cells (CTCs) isolated from a blood sample from the subject; determine a measured CTC size distribution of the plurality of CTCs based on said measurements received; compare the measured CTC size distribution to a reference CTC size distribution; and assign the disease condition of the cancer of the subject based on the comparing.

Some embodiments of the present invention include computer-readable mediums comprising non-transient computer-executable code for assessing a disease condition of a cancer of a subject, the non-transient computer-executable code, when executed by a computer, causes the computer to perform steps comprising: receive measurements of at least one of cell sizes or cell nucleus sizes for each of a plurality of circulating tumor cells (CTCs) isolated from a blood sample from the subject; determine a measured CTC size distribution of the plurality of CTCs based on the measurements received; compare the measured CTC size distribution to a reference CTC size distribution; and assign said disease condition of the cancer of the subject based on the comparing.

Some embodiments of the present invention are directed to methods, systems and computer readable mediums for assigning a metastatic stage of a cancer. In some embodiments directed to methods, systems and computer readable mediums for assigning a metastatic stage of said cancer, assigning the metastatic stage of the cancer comprises assigning a visceral metastatic stage based at least on a component of very-small-nuclear CTCs in said measured CTC size distribution.

Some embodiments of the present invention are directed to methods, systems and computer readable mediums for assessing a disease condition of a cancer of a subject by, in part, measuring a longest dimension of each of isolated CTCs, measuring a dimension perpendicular to each corresponding longest axis, taking a product of each longest dimension and corresponding perpendicular dimensions, and taking the square root of each said product.

In some embodiments of the present invention directed to methods and systems for assessing a disease condition of a cancer of a subject, a device is used to isolate a plurality of CTCs and has a nanostructured surface that enhances capture of the CTCs preferentially over other types of cells. Such a device is illustrated schematically in FIG. 1B and described in U.S. Pat. No. 9,140,697, the entire contents of which are hereby incorporated by reference. The device (100) contains a substrate (102) having a nanostructured surface region (104). A plurality of binding agents (106) is attached to said nanostructured surface region of said substrate. The nanostructured surface region comprises a plurality of nanostructures (such as nanostructure 108) each having a longitudinal dimension and a lateral dimension. As a sample is placed on the device, biological cells (110) are selectively captured by the binding agents and the plurality of nanostructures acting in cooperation. More cell surface components attach onto nanostructured substrates than flat substrates because nanostructured substrates provide enhanced local interaction with cell surface components.

In some embodiments directed to methods and systems for assessing a disease condition of a cancer of a subject, a NanoVelcro cell-affinity assay is used, by which anti-EpCAM (epithelial cell adhesion molecule)-coated nanostructured substrates (e.g., vertically oriented silicon nanowire substrates, SiNWS) are utilized to capture CTCs in a stationary device setting with a capture efficiency ranging from 40 to 70%. (See, for example, U.S. Published Patent Application No. US 2012/0003711 A1, "Device for Capturing Circulating Tumor Cells," and U.S. Published Patent Application No. US 2015-0260710A1, "Selective Capture and Stimulated Release of Circulating Tumor Cells on Nanostructured Devices," both of which are assigned to the same assignee as the current application, the entire contents of each of which are incorporated herein by reference.) A unique feature of the NanoVelcro CTC assay is the use of a nanostructured substrate. The enhanced local topographic interactions between the SiNWS and nano-scaled cellular surface components (e.g., microvilli) are analogous to the working principle of nanoscale VELCRO, resulting in a vastly improved cell-capture affinity compared to that observed for non-structured (i.e., flat) substrates. The general applicability of the NanoVelcro concept is supported by i) recent studies, where it was demonstrated that other types of nanostructured substrates, e.g., electrochemically deposited conjugated polymer nano-features, and horizontally packed ultra-long TiO2 nanofibers, also exhibit synergistic effects in conjunction with capture agents to achieve enhanced CTC-capture performance, and ii) studies, where immune cell-specific capture agent-coated SiNWS were utilized to sort subpopulations of immune cells. (See also "Systems, Methods and Components for Isolating Cells from a Fluid Sample," PCT/US13/43171, filed May 29, 2013, assigned to the same assignee as the current application, the entire contents of which are incorporated herein by reference.)

1. Definitions

To facilitate an understanding of the present invention, a number of terms and phrases are defined below.

As used herein, the singular forms "a", "an", and "the" include plural forms unless the context clearly dictates otherwise. Thus, for example, reference to "a binding agent" includes reference to more than one binding agent.

The term "nanostructure" refers to a structure having a lateral dimension and a longitudinal dimension, wherein the lateral dimension, the longitudinal dimension, or both the lateral and longitudinal dimensions are less than 1 mm. The shape of the nanostructure is not critical. It can, for example, be any three dimensional surface such as a bead, particle, strand, tube, sphere, etc.

The terms "diagnostic" and "diagnosis" refer to identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

The terms "subject", "patient" or "individual" generally refer to a human, although the methods of the invention are not limited to humans, and should be useful in other mammals (e.g., cats, dogs, etc.).

"Sample" is used herein in its broadest sense. A sample may comprise a bodily fluid including blood, serum, plasma, tears, aqueous and vitreous humor, spinal fluid, urine, and saliva; a soluble fraction of a cell or tissue preparation, or media in which cells were grown. Means of obtaining suitable biological samples are known to those of skill in the art.

The term "binding agent" as used herein refers to any entity or substance, e.g., molecule, which is associated with (e.g., immobilized on, or attached either covalently or non-covalently to) the nanostructured surface region, or which is a portion of such surface (e.g., derivatized portion of a plastic surface), and which can undergo specific interaction or association with the target cell. A "plurality of binding agents" can refer to a plurality of one particular binding agent or a plurality of more than one binding agent.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, hybrid antibodies, fusion proteins comprising an antibody portion, and any other modified immunoglobulin molecule comprising an antigen recognition site so long as the antibodies exhibit the desired biological activity. An antibody may be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies may be naked or conjugated to other molecules such as toxins, radioisotopes, etc.

The term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

"Hybrid antibodies" are immunoglobulin molecules in which pairs of heavy and light chains from antibodies with different antigenic determinant regions are assembled together so that two different epitopes or two different antigens may be recognized and bound by the resulting tetramer.

"Isolated" in regard to cells, refers to a cell that is removed from its natural environment (such as in a solid tumor) and that is isolated or separated, and is at least about 30%, 50%, 75%, and 90% free from other cells with which it is naturally present, but which lack the marker based on which the cells were isolated.

That a molecule (e.g., binding agent) "specifically binds" to or shows "specific binding" or "captures" or "selectively captures" a target cell means that the molecule reacts or associates more frequently, more rapidly, with greater duration, and/or with greater affinity with the target cell than with alternative substances. Thus, under designated experimental conditions, the specified molecule bind to the target cell at least two times the background and does not substantially bind in a significant amount to other cells and proteins present in the sample.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

EXAMPLES

The following examples help explain some concepts of the current invention. However, the general concepts of the current invention are not limited to the particular examples.

Figure 1B:
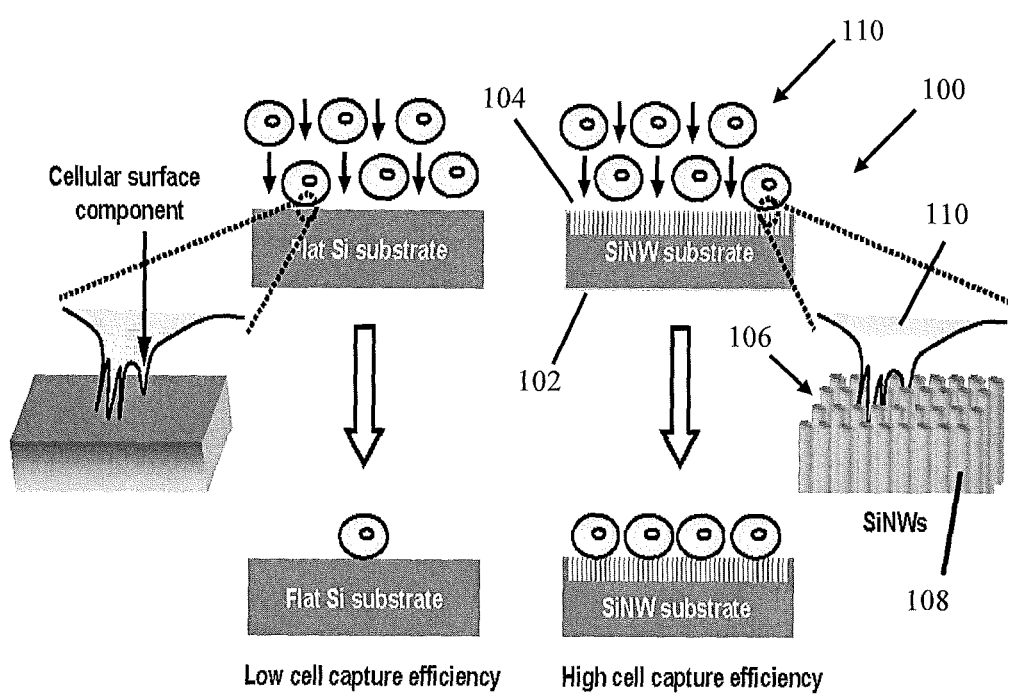
FIG. 1B shows an illustration of a device used to isolate circulating tumor cells having a nanostructured surface

Example 1: Very-Small-Nuclear Circulating Tumor Cell (vsnCTC) as a Diagnostic Biomarker for Visceral Metastasis in Advanced Prostate Cancer In this example, we recruited PC patients encompassing a broad clinical spectrum of the disease including no metastasis, bone/lymph node metastasis only, and visceral metastasis present, aiming to find the characteristics of visceral metastasis in CTCs. FIG. 1A shows a schematic of the study design (scale bars are 10 micrometers). CTC enumeration studies were performed for these patients using highly sensitive NanoVelcro Chips [24, 25] in conjunction with the fluorescence microscopy to identify CTCs by the conventional criteria (DAPI+/CK+/CD45−). The nuclear sizes of the identified CTCs were measured and subjected to statistical modeling, by which we identified three subpopulations of CTCs, termed large-nuclear CTCs (lnCTCs), small-nuclear CTCs (snCTCs) and very-small-nuclear CTCs (vsnCTCs). Significant correlation was found between the CTC subpopulations and metastatic status as the snCTCs and vsnCTCs together (snCTCs+vsnCTCs) and vsnCTCs counts alone predict with the presence of metastatic PC and aggressive metastatic PC with visceral involvement, respectively. Moreover, serial enumerations of index patients suggested the potential role of vsnCTCs for predicting the onset of visceral metastasis and monitoring treatment response. The analysis of cellular markers shows a biochemical similarity between vsnCTCs and neuroendocrine PC. These findings indicate the presence of vsnCTCs as a characteristic of PC with visceral metastasis, and may serve as a diagnostic marker for this most aggressive form of PC.

Patients and Methods

Patients and Samples

All the patients had histologically confirmed PC and underwent evaluation and/or treatment at Cedars-Sinai Medical Center (CSMC). Sample collections and analyses were approved by the CSMC Institutional Review Board. For those patients at risk of having metastatic disease, imaging within 3 months of sample collection was required for inclusion. Multiple blood draws from individual patients was allowed. Venous blood was collected for this study in acid-citrate dextrose-containing vacutainers (BD Bioscience) and processed within 4 hours of collection.

CTC Enrichment Using NanoVelcro Chips

The general protocol for CTC enrichment by NanoVelcro Chips is briefly summarized: 1.0 mL of venous blood was subjected to red blood cells (RBC) depletion using a standard RBC lysis buffer (containing $NH_4Cl$ and Tris, pH 7.2); remaining cells were incubated with the capture agents (biotinylated goat anti-human EpCAM antibody, R&D Systems); after washing carefully, the sample was loaded into the NanoVelcro Chip, which consists of a streptavidin-coated NanoVelcro substrate and an overlaid PDMS chaotic mixer. In conjunction with the use of an automated fluid handler, the cell suspension was introduced into the Chip at a consistent flow rate (0.5 mL/h). After fixation by 2% paraformaldehyde (PFA, Electron Microscopy Science), the cells immobilized on the NanoVelcro substrate were subjected to immunocytochemical (ICC) staining with DAPI, FITC-conjugated anti-CK, and TRITC-conjugated anti-CD45, and subsequent microscopy imaging to identify the CTCs.

CTC Imaging Followed by Nuclear Size Measurements

The imaging system consists of an upright fluorescence microscope (Eclipse 90i, Nikon) with NIS-Element imaging software (Nikon). An automatic scan over the NanoVelcro chip was carried out by the imaging system under 40× magnification with DAPI, FITC and TRITC channels corresponding to nuclear, CK, and CD45 staining, respectively. The DAPI+/CK+/CD45− events (FIG. 1A) were defined as the CTC candidates and subjected to subsequent automatic scan at either 100× or 400× magnification. The high-resolution images were reviewed by an experienced technician and a senior pathologist to exclude any false identification. For all the CTCs passing final review, the nuclear size was measured along the longest axis and the width perpendicular to that axis (FIG. 1A). [26, 27] The nuclear size for statistical analyses is defined as follows:

$$\text{nuclear size} = \sqrt{(\text{longest axis}) \times (\text{perpendicular width})}$$

To ensure the consistency and accuracy of nuclear size measurements on NanoVelcro Chips, we performed a series of calibration studies using PC cell lines and their spiked blood samples.

Statistical Analyses

To identify the subpopulations of CTCs, we performed cluster analysis for the CTC nuclear sizes using the Gaussian Mixture Model (GMM) formed by K Gaussian components with varied variances. The means and variances of K Gaussian components are estimated by Expectation-Maximization (EM) algorithm and the optimal number K was decided by Akaike information criterion and Bayesian information criterion. Then we can classify CTCs into K clusters based on their nuclear sizes, where a CTC will be assigned to the cluster with the maximum likelihood amount all K Gaussian components.

Wilcoxon tests were used to evaluate the statistical differences of CTC counts between different metastatic categories: 1) metastasis versus no metastasis and 2) non-visceral metastasis versus visceral metastasis present. The distributions of CTC counts are visualized using box plots. Receiver operating characteristic (ROC) curves were used to compare the diagnostic performances of the CTC counts corresponding to different clusters. The areas under the ROC curves were computed with 95% confidence intervals (CIs). All tests are two-sided and P values less than 0.05 were considered statistically significant. All statistical tests were performed using the R software.

Results

PC Patient Recruitment, Characteristics, and Sample Collections for CTC Enumeration Studies Fresh venous blood samples for CTC enumeration were collected from PC patients treated at CSMC between January 2013 and June 2014. A total of 50 patients from a broad clinical course of PC were identified to have samples usable from this analysis from our various blood collection protocols. In brief, this study included patients receiving primary local therapy (i.e. radical prostatectomy or primary radiotherapy), patients receiving adjuvant therapy (chemotherapy or salvage radiotherapy), patients under active surveillance, castration sensitive patients receiving androgen deprivation therapy (ADT), and metastatic castration resistant patients (mCRPC) receiving systemic therapies. Patient samples were categorized by sites of metastases: 1) no metastasis, 2) bone/lymph node metastasis only, and 3) visceral metastases present.

Statistical Analysis and Modeling of CTC Nuclear Size Distribution and CTC Subpopulations A total of 254 CTCs identified in 92 enumeration studies (from 50 patients) was used for the statistical analysis and modeling of the distribution of CTC nuclear sizes. FIG. 2 shows graphs depicting results from the statistical analysis and modeling of CTC nuclear size distribution and CTC subpopulations. The histogram in FIG. 2, panel A depicts the distribution of 254 CTCs according to their nuclear sizes. The black solid line shows the density of the optimal Gaussian mixture model (GMM) that best fits the histogram. Lines 21, 22 and 23 represent the three cluster-specific Gaussian density curves (Groups 1, 2 and 3), respectively. The dash lines indicate the cutoffs of our classification rule: assigning a sample to the cluster with the maximum Gaussian likelihood. In FIG. 2, panel B, line 24 shows the Akaike information criterion (AIC) values and line 25 shows the Bayesian information criterion (BIC) values for K (cluster number) from 1 to 5. The best cluster number is 3 as both AIC and BIC reached the minimum when K=3.

Figures 2A, 2B:
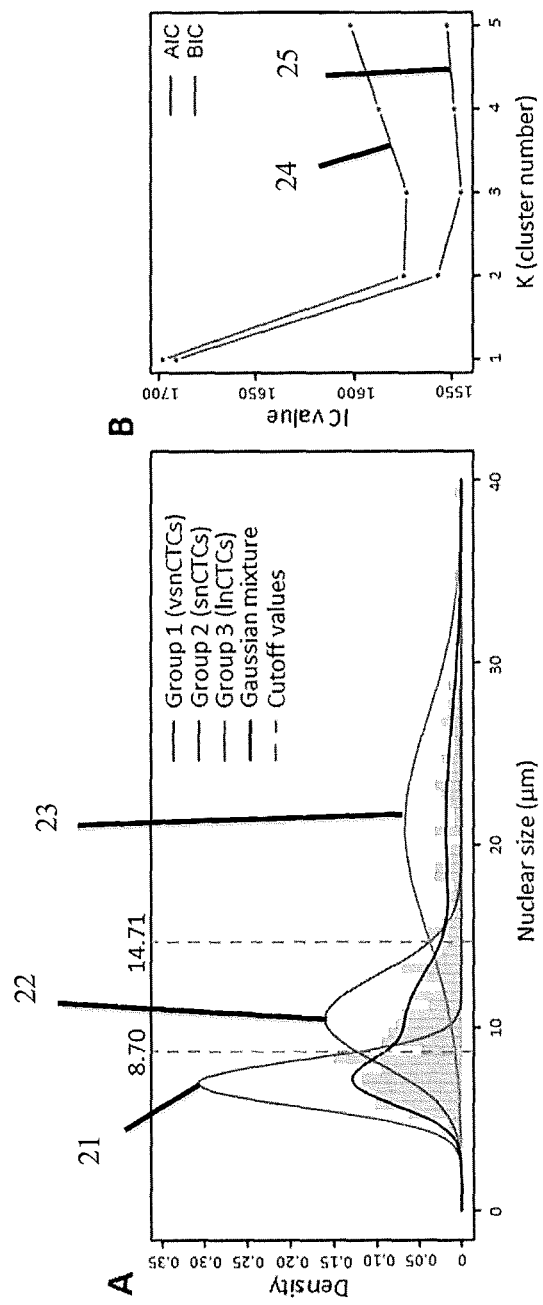
FIGS. 2A-2B show graphs depicting results from the statistical analysis and modeling of Circulating Tumor Cells (CTC) nuclear size distribution and CTC subpopulations.

Based on the information criterion AIC and BIC, the optimal model is a 3-cluster GMM with cluster means (6.94, 10.49, 21.04 μm), standard deviations (1.30, 2.49, 5.91 μm) and prior probabilities (0.34, 0.38, 0.28) (FIG. 2A). The AIC and BIC values of different cluster number are also shown (FIG. 2B). We then assigned CTCs into the cluster with the maximum Gaussian likelihood, and yielded three CTC subpopulations that we labeled as very-small-nuclear CTCs (vsnCTCs, nuclear size <8.70 μm), small-nuclear CTCs (snCTCs, nuclear size between 8.70 μm and 14.71 μm) and large-nuclear CTCs (lnCTCs, nuclear size >14.71 μm).

Relationship Between CTC Nuclear Sizes and Metastatic Status

Figures 3A, 3B, 3C, 3D:
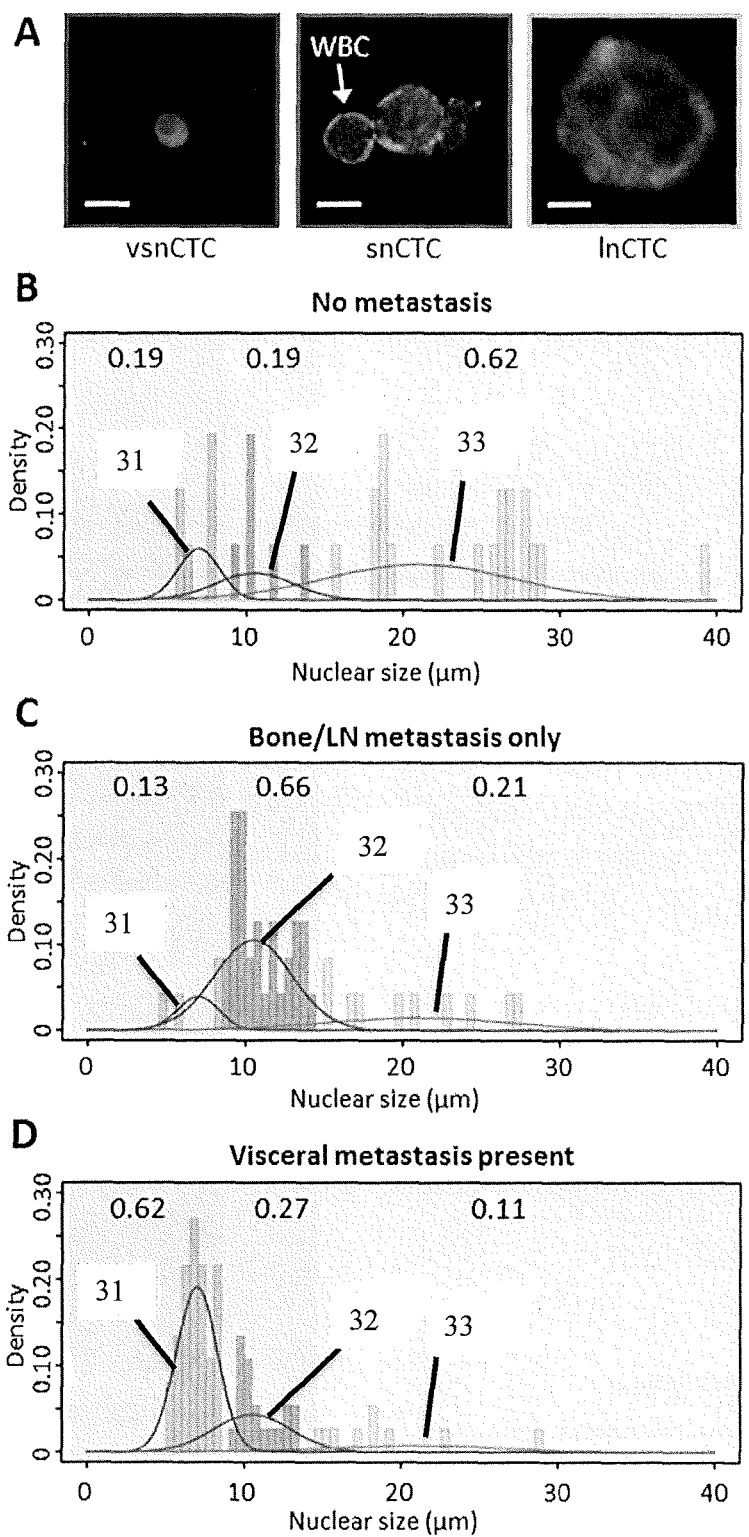
FIGS. 3A-3D show fluorescent images of various CTCs and data graphs showing the relationship between CTC nuclear sizes and metastatic status.

To further analyze the relationship between the three CTC subpopulations and metastatic status, we first conducted a screening to filter out the CTCs and enumeration results that may be affected by treatments. Several patients who provided specimens underwent a number of therapeutic maneuvers with a variety of responses (examples of which are provided below). Some of these patients experienced clinical benefit from therapy. To eliminate the potential bias resulting from treatment effect [25, 28], samples obtained within 1 month of starting therapy were excluded from the analyses detailed below. Additionally, if there was clear benefit, samples relating to disease state were excluded until it was clear that the disease was progressing on treatment (i.e. risk of any treatment effect was minimized) Finally, if there was a paucity of contemporary imaging information that clarified the disease status at the time of the draw, samples were excluded from the re-analysis of the sample set (analytic set). In this analytic set, a total of 36 of the original 92 enumerations (38%) were excluded for potential treatment effect. A total of 152 CTCs from 56 enumeration tests were used for analyzing the relationship of CTC nuclear size and metastatic status. Histograms were plotted using CTC counts versus nuclear sizes and classified by metastatic status (FIGS. 3A-3D). FIGS. 3A-3D show fluorescent images of various CTCs and data graphs showing the relationship between CTC nuclear sizes and metastatic status. FIG. 3A shows representative images of lnCTC, snCTC and vsnCTC taken by fluorescence microscopy. The cells are stained with DAPI, FITC-conjugated anti-CK, and TRITC-conjugated anti-CD45. Histograms and cluster-specific Gaussian density curves were plotted using CTC counts versus nuclear sizes and classified into three metastatic statuses: FIG. 3B represents the category of no metastasis, in which lnCTCs account for the largest proportion (62%) among all the CTCs; FIG. 3C represents the category of bone/LN metastasis only, in which snCTC constitutes the major subpopulation (66%); and FIG. 3D represents the category of visceral metastasis present, in which vsnCTCs account for the largest proportion (62%), followed by snCTCs (27%). The proportions of the three CTC subpopulations varied significantly between different metastatic status as demonstrated by two-sided $\chi^2$ test (p=2.85×10$^{-13}$). In FIGS. 3B, 3C and 3D, lines 31, 32 and 33 represent vsnCTCs, snCTCs or lnCTCs, respectively.

The proportions of the three subtypes (examples in FIG. 3A) varied significantly between different statuses. In the category of no metastasis (FIG. 3B), the majority of cells were classified as lnCTCs (62%). In the category of bone/

LN metastasis only (FIG. 3C), the majority of cells were classified as snCTC (66%). In the category of visceral metastasis present (FIG. 3D), the vsnCTCs constitute the major CTC subpopulation (62%), followed by snCTCs (27%). This result shows that our unsupervised clustering of CTCs has significant dependency to metastatic categories (two sided $\chi^2$ test, p=2.85×10$^{-13}$).

snCTC+vsnCTC Counts Correlate with Metastasis

Figures 4A, 4B, 4C, 4D:
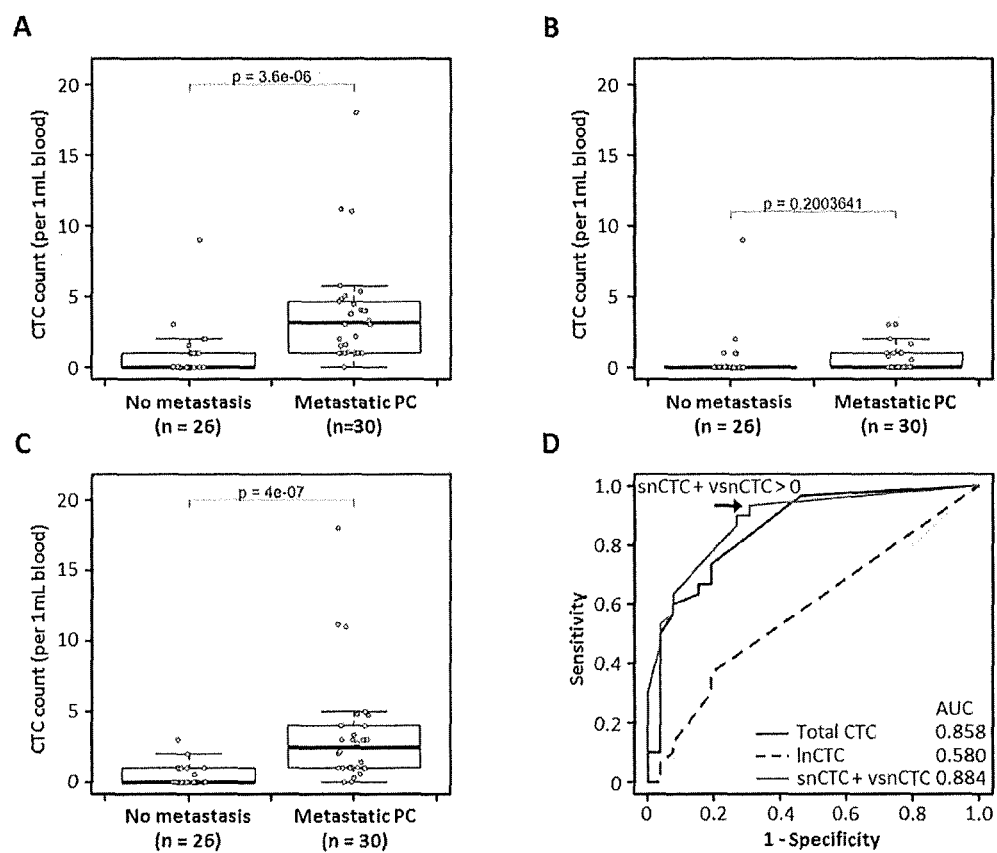
FIGS. 4A-4D show data graphs demonstrating the correlation between small nuclear CTC+very small nuclear CTC counts and metastatic PC.

Based on the observed relationship of CTC subpopulations and metastatic status, we then evaluated the diagnostic potential of different CTC subpopulations for metastatic PC. We performed a statistical analysis for the 56 enumeration tests that passed the aforementioned sample pool refinement, which resulted in 26 enumerations from the no metastasis category, and 30 from metastatic PC (bone/LN metastasis only+visceral metastasis present). FIGS. 4A-4D show data graphs demonstrating the correlation between snCTC+vsnCTC counts and metastatic PC. Box plots are shown for total CTC counts (FIG. 4A), lnCTC counts (FIG. 4B), and snCTC+vsnCTC counts in 1.0 mL of blood (FIG. 4C). Boxes represent interquartile range, and the horizontal line across each box indicates median value. The y-axis represents CTC counts per mL of blood. There are 26 enumerations from the category of no metastasis and 30 from metastatic PCs in the analyses. Statistical analysis was performed using two-sided Wilcoxon test. All the p values are indicated in figures. FIG. 4D shows receiver operating characteristics (ROC) curves were generated using counts of CTC subpopulations for identifying metastatic PC. Total CTC count (lnCTCs+snCTCs+vsnCTCs, black line) yielded an area-under-curve (AUC) value of 0.856 (95% confidence interval [CI]=0.757 to 0.955) in identifying metastatic PCs. lnCTC counts (black dashed line) yielded an AUC value of 0.580 (95% confidence interval [CI]=0.460 to 0.700). snCTC+vsnCTC counts (line indicated by black arrow) yielded an AUC value of 0.884 (95% confidence interval [CI]=0.799 to 0.968).

Total CTC count (lnCTC+snCTC+vsnCTC) showed a statistically significant difference between metastatic and non-metastatic disease (0.94±1.84 versus 3.81±3.77 cells per mL of blood, p<0.001, FIG. 4A). However, as we separated the CTC subpopulations in statistical analyses, the lnCTC subpopulation failed to distinguish metastatic and non-metastatic disease (0.54±1.79 versus 0.53±0.87 cells per mL of blood, p=0.200, FIG. 4B). snCTC+vsnCTC counts, in contrast, remained significantly different (0.41±0.75 versus 3.28±3.87 cells per mL of blood, p<0.001, FIG. 4C). The ROC curves were generated to assess the potential usefulness of CTC count as a diagnostic biomarker for metastatic PC. snCTC+vsnCTC counts showed a larger area-under-curve (AUC) compared to total CTC count (0.884 versus 0.856, FIG. 4D). The sensitivity and specificity for diagnosing metastatic PC reached 69% and 93%, respectively, when using the cutoff of snCTC+vsnCTC count>0 cells per mL of blood. These results are consistently with the clustering of snCTCs and vsnCTCs in the histograms for bone/LN metastasis only and visceral metastasis present categories (see FIGS. 3C and 3D, respectively). This suggests that snCTC+vsnCTC counts may be a superior biomarker for metastasis compared to total CTC count.

vsnCTC Counts Correlate with the Presence of Visceral Metastasis

Figures 5A, 5B, 5C, 5D:
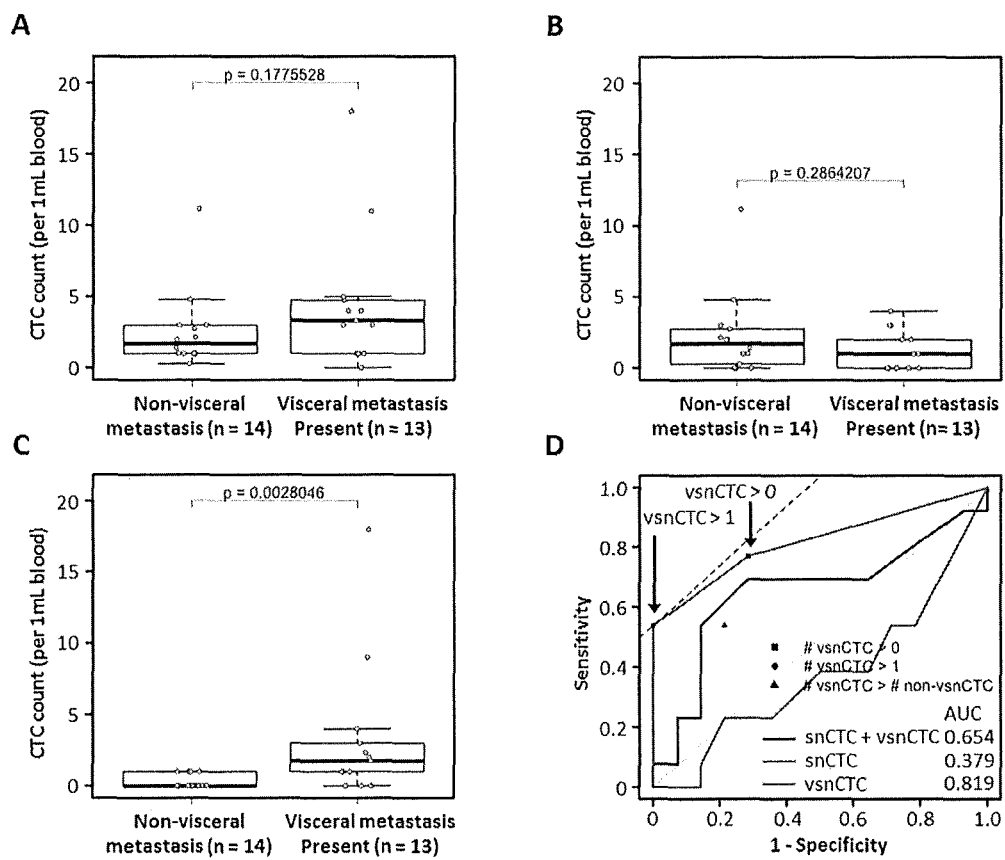
FIGS. 5A-5D show graphs demonstrating the correlation between vsnCTC counts and the aggressive PCs with visceral metastasis.

Next, we examined the diagnostic potential of the identified CTC subpopulations in detection of aggressive PC variants with visceral metastases. FIGS. 5A-5D show graphs demonstrating the correlation between vsnCTC counts and the aggressive PCs with visceral metastasis. Box plots are shown for snCTCs+vsnCTC counts (FIG. 5A), snCTC counts (FIG. 5B), and vsnCTC counts in 1.0 mL of blood (FIG. 5C). Boxes represent interquartile range, and the horizontal line across each box indicates median value. The y-axis represents CTC counts per mL of blood. A subset of samples from patients with known bone metastases were used for this analysis. These included 14 enumerations from the categories of non-visceral metastases (bone/LN metastasis only) and 13 enumerations from that of visceral and bone metastases in the analyses. Statistical analysis was performed using two-sided Wilcoxon test. All the p values are indicated in figures. FIG. 5D shows ROC curves were generated using counts of CTC subpopulations for identifying the presence of visceral metastases among metastatic PCs. snCTC+vsnCTC count (black line) yielded an AUC value of 0.654 (95% confidence interval [CI]=0.367 to 0.803) in identifying the presence of visceral metastasis among metastatic PCs. Count of snCTCs yielded an AUC value of 0.379 (95% confidence interval [CI]=0.167 to 0.570). Count of vsnCTC yielded an AUC value of 0.819 (95% confidence interval [CI]=0.606 to 0.921).

Though successful in distinguishing metastatic PC from no metastasis, snCTC+vsnCTC counts failed to identify visceral metastasis among the patients with bone/LN metastasis (2.54±2.75 versus 4.54±4.90 cells per mL of blood, p=0.178, FIG. 5A). Recognizing the preferential distribution of snCTCs and vsnCTCs in FIG. 3D, we pursued further statistical analyses of individual CTC subpopulations. The results showed that snCTCs alone were unable to identify visceral metastases among the patients with bone/LN metastasis (2.26±2.91 versus 1.23±1.42 cells per mL of blood, p=0.286, FIG. 5B). However, vsnCTC counts successfully distinguished visceral metastasis from non-visceral-metastatic PC (0.29±0.47 versus 3.31±5.02 cells per mL of blood, p=0.0028, FIG. 5C). ROC curves showed a larger AUC for vsnCTCs (0.819) compared to both snCTCs alone (0.379) and the combination of both subpopulations (0.654, FIG. 5D). The sensitivity and specificity for diagnosing visceral metastasis reached 77% and 71%, respectively, when the applied cutoff value for vsnCTC count is >0 cells per mL. The highest sum of sensitivity and specificity occurs when the cutoff for vsnCTC count was set at >1 per ml of blood. The sensitivity and specificity was 54% and 100%, respectively. This result demonstrates the potential of vsnCTC counts as a diagnostic marker for aggressive PC with visceral involvement.

Individual Clinical Cases: Correlation Between vsnCTC and Visceral Metastasis

To present the value of serial sample analysis, we present two clinical cases with important changes in their natural history with their change in vsnCTC counts during their period of following up:

Patient A: Prediction of New Lung Metastasis.

This patient presented with a locally advanced, high grade PC that relapsed and progressed to metastatic castration resistant PC (mCRPC). He was treated with a series of systemic therapies including abiraterone acetate, docetaxel, radium-223, and an experimental PI3K inhibitor. He experienced limited biochemical and clinical benefit from therapy and eventually developed a pulmonary metastasis followed by rapid clinical deterioration and death.

Figures 6A, 6B:
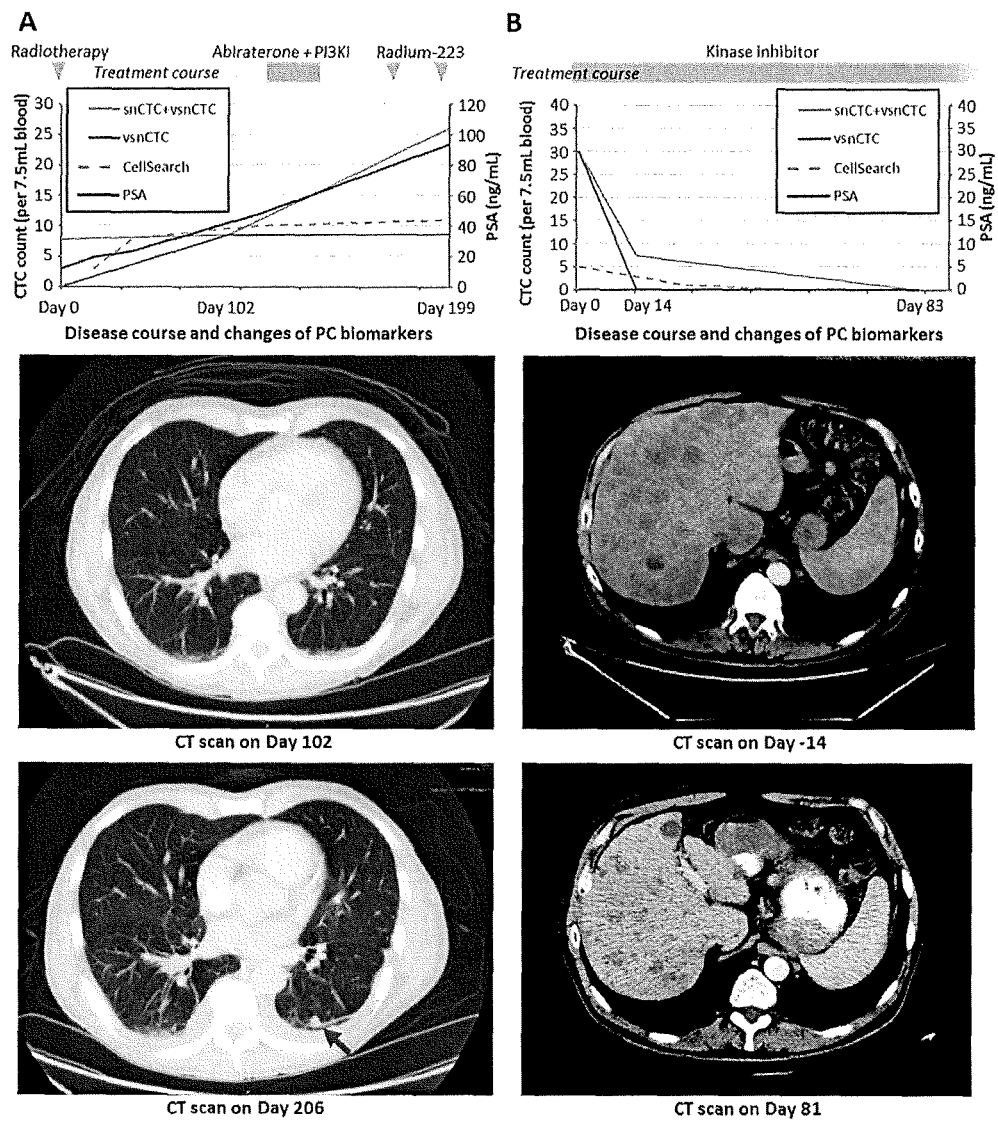
FIGS. 6A-6B show data plots and images of computed tomography (CT) scans from clinical cases, where the serial CTC enumerations show the correlation between vsnCTC count and visceral metastasis.

FIGS. 6A-6B show data plots and images of CT scans from clinical cases, where the serial CTC enumerations show the correlation between vsnCTC count and visceral metastasis. FIG. 6A shows the disease course of Patient A who had metastatic castration-resistant prostate cancer (mCRPC). The patient started to receive NanoVelcro CTC enumeration tests with at disease status of bone metastasis (confirmed by bone scan). No visceral metastasis was found upon survey. During serial CTC enumerations, vsnCTC was detected on Day 102, about three months prior to detection of a new metastatic lesion in the lung by CT scan on Day 206. FIG. 6B shows disease course of Patient B who had mCRPC and biopsy-confirmed liver metastases. Serum PSA concentrations were below 1.0 ng/mL and CellSearch assays measured ≤5 CTCs/7.5 mL throughout his clinical course. His initial vsnCTC count was equivalent to 30 vsnCTCs in 7.5 mL of blood. The vsnCTCs became undetectable in serial CTC enumerations after starting an experimental kinase inhibitor, and CT scans showed the regression of his liver metastasis at Day 81. The bone disease was also found regressing by bone scan.

At the outset of the serial CTC analysis, imaging by CT and bone scan confirmed that his macroscopic disease burden was limited to osseous spread (FIG. 6A). We identified the emergence of vsnCTCs, which preceded the development of the lung metastasis by approximately 100 days. These vsnCTC persisted for the remainder of his disease course. This event was not accompanied by pulmonary symptomatology. This case suggests that vsnCTCs may be a predictive marker for the development of visceral metastasis.

Patient B: Monitoring Clinical/Radiographic Response.

This was a mCRPC patient with known liver metastases that developed early in his natural history. His disease progressed radiographically (without rising serum PSA concentration) despite ADT and docetaxel. He began CTC collections during participation on a clinical trial with an investigational multi-targeted kinase inhibitor. The patient experienced a clinical improvement within 2 weeks of starting therapy and soft tissue and bone response was noted at 3 months (FIG. 6B).

At his first draw this patient was found to have 30 CTCs/7.5 mL identified by the NanoVelcro Chip (versus 5 CTCs/7.5 mL by CellSearch), all of which were vsnCTCs. Within 2 weeks of starting therapy, his CTC counts were 7.5 snCTCs/7.5 mL and 0 vsnCTCs/7.5 mL. The CTC counts have further declined and he continues to benefit therapy at the time of this publication. The disappearance of vsnCTCs correlated well with the regression of his liver metastases, suggesting the potential role of vsnCTC in dynamic monitoring of disease response for patients with preexisting visceral metastases including those who are not able to be surveilled by conventional blood-based diagnostics.

Correlation of Marker Expression Between vsnCTCs and Metastatic Tumor Tissues

Figures 7A, 7B:
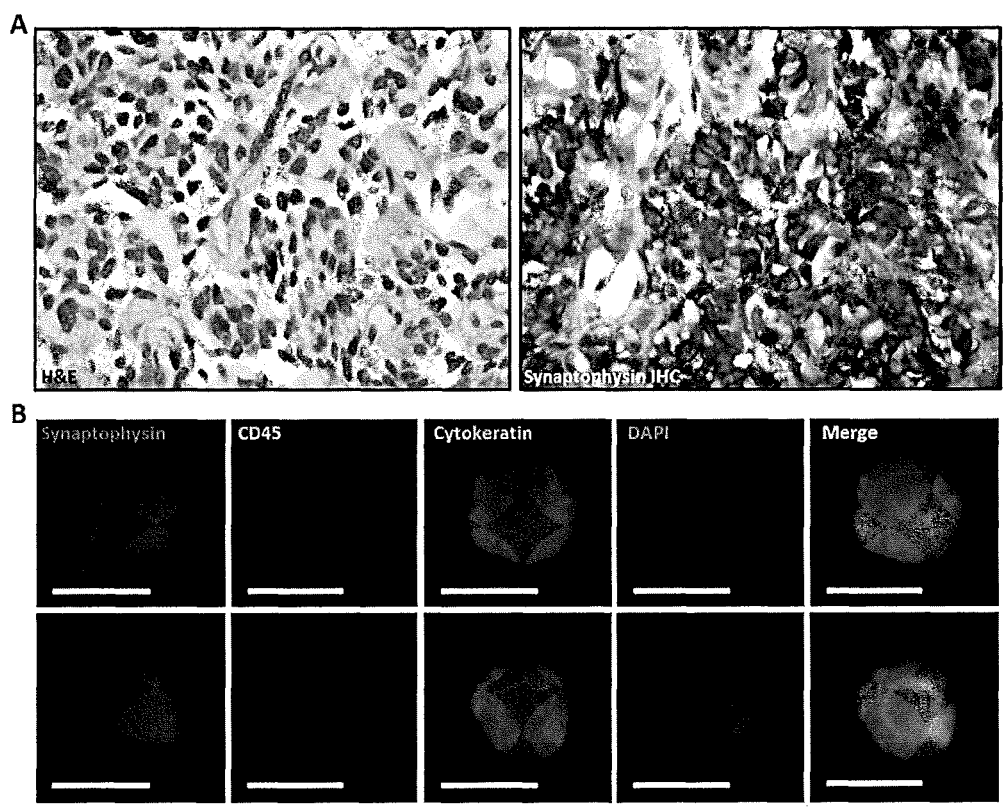
FIGS. 7A-7B are panels of images showing immunohistochemical staining of vsnCTCs and metastatic tumor tissues.

To further evaluate the association between vsnCTCs and the metastatic tumors in visceral organs, we compared the expression of several cellular markers in CTCs and a contemporary metastatic tumor biopsy from Patient C. Patient C was pathologically diagnosed with small cell (neuroendocrine) carcinoma of prostate with a serum PSA of 6.8 ng/mL. He relapsed 1 year after aggressive local therapy with prostatectomy, adjuvant radiotherapy, and platinum-based chemotherapy. At relapse he was found to have new lung and bone metastases without biochemical progression. This patient underwent biopsy of a pleural metastasis with a blood collection for CTC analysis. FIGS. 7A-7B are panels of images showing immunohistochemical staining of vsc-CTCs and metastatic tumor tissues. FIGS. 7A-7B show positive association between vsnCTCs and contemporary metastatic tumor tissues is demonstrated by shared cellular markers. FIG. 7A shows a representative cross-section of a metastatic PC tumor at pleural cavity. Left: standard H&E staining for pleural tumor biopsy; right: immunohistochemistry (IHC) analysis for synaptophysin expression in pleural tumor. FIG. 7B shows synaptophysin staining on vsnCTCs obtained contemporarily. The scale bars in the figures indicate 10 μm.

Histomorphology of the metastatic lesion is shown in FIG. 7A. Immunohistochemical (IHC) staining on the biopsy showed strong synaptophysin and cytokeratin expression. The same antibodies for synaptophysin and cytokeratin were used for CTCs, where synaptophysin and cytokeratin expression was also identified (FIG. 7B). The finding not only suggests that CTCs are derived from tumor tissues, but also lends the evidence that by incorporating additional markers, CTCs may provide insightful information adjunctive to pathologic analyses on tumor tissues and/or help distinguish pathologic subsets of PC, such as the small-cell carcinoma patient presented here.

Discussion

Histopathology remains the gold standard for cancer diagnosis. Distinction between benign and malignant tissues relies largely on the interpretation of pathologists. The concept of "quantitative pathology" was therefore introduced in late $20^{th}$ century aiming to measure and quantify the morphological features with standardized algorithms in software [29-31]. However, this approach has not been adopted broadly in modern medicine despite the research advances made over the past 20 years. Here, we imposed this underappreciated and fundamental concept to a highly sensitive and specific CTC enumeration approach based on NanoVelcro Chips, resulting in the identification of snCTC and vsnCTC subpopulations that can be regarded as diagnostic biomarkers for metastatic PCs and the aggressive PCs with visceral involvement.

As demonstrated in this study and in previous publications, NanoVelcro Chips exhibit high sensitivity in detecting CTCs from peripheral blood [24, 25]. Using fluorescence microscopy, we generated cell images that meet standards for quantitative pathology. This allows for highly specific identification of CTCs from surrounding WBCs, and at the same time enables nuclear size measurement for individual CTCs. Among the commonly used cellular features (e.g., cellular and nuclear shapes/sizes, nuclear/cytoplasmic contents), we found nuclear sizes to be the most robust feature for the NanoVelcro substrate-immobilized CTCs due to: 1) the high reproducibility of DAPI staining and 2) the minimal attenuation of DAPI fluorescence during the imaging process. Moreover, we acknowledge that in our experience and the reports of other groups, the cellular membrane of CTCs is extremely fragile and subject to generation of artifacts and disruption by mechanical forces [32]. In contrast, the nuclear morphology was rather well preserved during the entire CTC enumeration processes. Our observation was consistent with the historic findings of the importance of nuclear morphology and cancer stage and outcome [REF]. As a result, we focused on measuring the size of nuclei.

With the aid of technical advances, we identified three different subpopulations of CTCs by nuclear size, namely lnCTCs, snCTCs and vsnCTCs. snCTC+vsnCTC counts are significantly higher in metastatic PC than the no metastasis category. The ROC curve showed a superior diagnostic power compared to total CTC count or lnCTCs. The sensitivity and specificity for diagnosing metastatic PC reached 69% and 93%, respectively, when using the cutoff of snCTC+vsnCTC counts>0 cell per mL of blood. Furthermore, vsnCTCs were significantly higher in the aggressive PC with visceral involvement compared to other metastatic PCs. ROC curves showed a larger AUC for vsnCTCs (0.819)

compared to both snCTCs alone (0.379) and the combination of both subpopulations (0.654). The highest sum of sensitivity and specificity occurs when the cutoff for vsnCTC count was set at >1 cell per mL of blood. The sensitivity and specificity was 54% and 100%, respectively.

On top of the existing CTC enrichment technologies, significant research endeavors have been devoted to molecular characterizations targeting various genomic [33], transcriptomic [34, 35], and proteomic signatures [36, 37] in CTCs. In the classical literature of cancer cell biology, nuclear morphology and size correlate with variations in upstream molecular signals that are closely linked to cellular behaviors [22, 38, 39]. Only a few groups have described morphological features of CTCs [40] and mainly focused on cell size that may have affected the detection rate for CTCs in filter-based [41] technologies. We demonstrated in this study that nuclear size of CTCs allows for identification of vsnCTCs that exhibits diagnostic significance for the aggressive PC with visceral metastasis.

In addition to CTC nuclear size, we conducted immunostaining of CK and synaptophysin and found the presence of these markers in vsnCTCs and a contemporary pleural metastasis from our index patient. This bears particular import as synaptophysin is a recognized marker for neuroendocrine prostate cancer (NEPC) [4] that has not been previously reported in PC CTCs. This suggests that the vsnCTCs we identified may be derived from or share a common origin with the metastatic tumor. This also implies that additional cellular markers in CTCs could be used to provide information useful for distinguishing certain pathologic subtypes of PC.

There are several points of uniqueness that have paved the way for our findings. First, instead of the commonly used approaches that classify PC according to clinical stage, Gleason Score, or castration sensitivity, we categorized disease based on its metastatic capacity, focusing on lethal, visceral metastasis. Second, we recruited a cohort that contains not only patients from a broad clinical course of PC but also the rare patients with visceral metastases. Finally, rigorous statistical analysis and modeling were performed to identify CTC subpopulations.

Previous efforts have been largely devoted to the prognostic significance of CTCs. It has been demonstrated that elevated CTC counts obtained by CellSearch™ can predict overall survival of PC patients [11-18], and their response to certain therapies [42]. However, only a few studies showed the potential diagnostic value of CTCs for metastatic PC [18, 43, 44]. Based on our findings and current clinical guidelines, we would propose the potential utility of snCTCs and vsnCTCs detected by NanoVelcro Chips. The striking relationship between the detection of vsnCTCs and visceral metastases points toward a potential new clinical tool for monitoring patients with advanced mCRPC. Given the recent findings of ECOG 3805 (CHAARTED) [45][REF], consideration has been given to more aggressive treatment of PC at earlier stages as this study showed that early cytotoxic therapy significantly improved patient survival. At this time, visceral metastases are typically detected late in the disease course and are often followed quickly by the patient's demise. Early detection of patients with or at risk for visceral metastases would allow for early intervention that may significantly alter an otherwise fatal disease course. Such a tool may also impact the state of clinical research by identifying an optimal subject pool for implementation of novel therapeutic approaches that may enhance the clinical benefit of these new treatments.

In summary, we performed the NanoVelcro CTC enumeration assay on a broad spectrum of PC patients, and provided compelling evidence that CTC subpopulations defined by nuclear sizes exhibit clinical relevance. The NanoVelcro assay provides a high degree of sensitivity and specificity in CTC identification that makes nuclear size assessment possible and meaningful. Moving forward, large-scale prospective trials will be conducted to validate (i) the utility of combined snCTC and vsnCTC subpopulations as a diagnostic marker adjunctive to current diagnostic tools (i.e. bone scan and MRI) for detecting metastatic PC, and (ii) the unique diagnostic potential of vsnCTCs for the aggressive PC with visceral metastasis. Given the fundamental nature of morphologic analysis in pathology, we anticipate the utility of snCTCs and vsnCTCs to be incorporated into clinical practice guidelines and direct treatments or measure the efficacy of therapies in the future.

References for Example 1

1. Siegel R, Ma J, Zou Z, et al. Cancer statistics, 2014. *CA Cancer J Clin* 2014; 64(1):9-29.
2. Roodman G D. Mechanisms of bone metastasis. *N Engl J Med* 2004; 350(16):1655-64.
3. Halabi S, Kelly W K, Zhou H, et al. The site of visceral metastases (mets) to predict overall survival (OS) in castration-resistant prostate cancer (CRPC) patients (pts): A meta-analysis of five phase III trials. *J Clin Oncol* 32:5s, 2014 (suppl; abstr 5002).
4. Beltran H, Tomlins S, Aparicio A, et al. Aggressive Variants of Castration-Resistant Prostate Cancer. *Clin Cancer Res* 2014; 10.1158/1078-0432.CCR-13-3309.
5. Aparicio A M, Harzstark A L, Corn P G, et al. Platinum-based chemotherapy for variant castrate-resistant prostate cancer. *Clin Cancer Res* 2013; 19(13): 3621-30.
6. Papandreou C N, Daliani D D, Thall P F, et al. Results of a phase II study with doxorubicin, etoposide, and cisplatin in patients with fully characterized small-cell carcinoma of the prostate. *J Clin Oncol* 2002; 20(14):3072-80.
7. Beltran H, Tagawa S T, Park K, et al. Challenges in recognizing treatment-related neuroendocrine prostate cancer. *J Clin Oncol* 2012; 30(36):e386-9.
8. Yuan X, Cai C, Chen S, et al. Androgen receptor functions in castration-resistant prostate cancer and mechanisms of resistance to new agents targeting the androgen axis. *Oncogene* 2014; 33(22):2815-25.
9. Lipianskaya J, Cohen A, Chen C J, et al. Androgen-deprivation therapy-induced aggressive prostate cancer with neuroendocrine differentiation. *Asian J Androl* 2014; 10.4103/1008-682X.123669.
10. Danila D C, Fleisher M, Scher H I. Circulating tumor cells as biomarkers in prostate cancer. *Clin Cancer Res* 2011; 17(12):3903-12.
11. Goldkorn A, Ely B, Quinn D I, et al. Circulating tumor cell counts are prognostic of overall survival in SWOG S0421: a phase III trial of docetaxel with or without atrasentan for metastatic castration-resistant prostate cancer. *J Clin Oncol* 2014; 32(11):1136-42.
12. Resel Folkersma L, San Jose Manso L, Galante Romo I, et al. Prognostic significance of circulating tumor cell count in patients with metastatic hormone-sensitive prostate cancer. *Urology* 2012; 80(6): 1328-32.
13. Wang F B, Yang X Q, Yang S, et al. A higher number of circulating tumor cells (CTC) in peripheral blood indicates poor prognosis in prostate cancer patients—a meta-analysis. *Asian Pac J Cancer Prev* 2011; 12(10):2629-35.

14. Scher H I, Jia X, de Bono J S, et al. Circulating tumour cells as prognostic markers in progressive, castration-resistant prostate cancer: a reanalysis of IMMC38 trial data. *Lancet Oncol* 2009; 10(3):233-9.
15. Olmos D, Arkenau H T, Ang J E, et al. Circulating tumour cell (CTC) counts as intermediate end points in castration-resistant prostate cancer (CRPC): a single-centre experience. *Ann Oncol* 2009; 20(1):27-33.
16. de Bono J S, Scher H I, Montgomery R B, et al. Circulating tumor cells predict survival benefit from treatment in metastatic castration-resistant prostate cancer. *Clin Cancer Res* 2008; 14(19):6302-9.
17. Moreno J G, Miller M C, Gross S, et al. Circulating tumor cells predict survival in patients with metastatic prostate cancer. *Urology* 2005; 65(4):713-8.
18. Thalgott M, Rack B, Maurer T, et al. Detection of circulating tumor cells in different stages of prostate cancer. *J Cancer Res Clin Oncol* 2013; 139(5):755-63.
19. Pantel K, Alix-Panabieres C. The potential of circulating tumor cells as a liquid biopsy to guide therapy in prostate cancer. *Cancer Discov* 2012; 2(11):974-5.
20. Khan M A, Walsh P C, Miller M C, et al. Quantitative alterations in nuclear structure predict prostate carcinoma distant metastasis and death in men with biochemical recurrence after radical prostatectomy. *Cancer* 2003; 98(12): 2583-91.
21. Mohler J L, Figlesthaler W M, Zhang X Z, et al. Nuclear shape analysis for the assessment of local invasion and metastases in clinically localized prostate carcinoma. *Cancer* 1994; 74(11):2996-3001.
22. Zink D, Fischer A H, Nickerson J A. Nuclear structure in cancer cells. *Nat Rev Cancer* 2004; 4(9):677-87.
23. Haber D A, Velculescu V E. Blood-based analyses of cancer: circulating tumor cells and circulating tumor DNA. *Cancer Discov* 2014; 4(6):650-61.
24. Wang S, Liu K, Liu J, et al. Highly efficient capture of circulating tumor cells by using nanostructured silicon substrates with integrated chaotic micromixers. *Angew Chem Int Ed Engl* 2011; 50(13):3084-8.
25. Lu Y T, Zhao L, Shen Q, et al. NanoVelcro Chip for CTC enumeration in prostate cancer patients. *Methods* 2013; 64(2): 144-52.
26. Klingauf M, Stanek D, Neugebauer K M. Enhancement of U4/U6 small nuclear ribonucleoprotein particle association in Cajal bodies predicted by mathematical modeling. *Mol Biol Cell* 2006; 17(12):4972-81.
27. Vesalainen S, Lipponen P, Talja M, et al. Nuclear morphometry is of independent prognostic value only in T1 prostatic adenocarcinomas. *Prostate* 1995; 27(2):110-7.
28. Kalykaki A, Agelaki S, Kallergi G, et al. Elimination of EGFR-expressing circulating tumor cells in patients with metastatic breast cancer treated with gefitinib. *Cancer Chemother Pharmacol* 2014; 73(4):685-93.
29. Baak J P. The principles and advances of quantitative pathology. *Anal Quant Cytol Histol* 1987; 9(2): 89-95.
30. Kayser G, Kayser K. Quantitative pathology in virtual microscopy: history, applications, perspectives. *Acta Histochem* 2013; 115(6):527-32.
31. Kothari S, Phan J H, Stokes T H, et al. Pathology imaging informatics for quantitative analysis of whole-slide images. *J Am Med Inform Assoc* 2013; 20(6):1099-108.
32. Lin M, Chen J F, Lu Y T, et al. Nanostructure Embedded Microchips for Detection, Isolation, and Characterization of Circulating Tumor Cells. *Acc Chem Res* 2014; 10.1021/ar5001617.
33. Lohr J G, Adalsteinsson V A, Cibulskis K, et al. Whole-exome sequencing of circulating tumor cells provides a window into metastatic prostate cancer. *Nat Biotechnol* 2014; 32(5):479-84.
34. Yu M, Bardia A, Aceto N, et al. Cancer therapy. Ex vivo culture of circulating breast tumor cells for individualized testing of drug susceptibility. *Science* 2014; 345(6193): 216-20.
35. Yu M, Bardia A, Wittner B S, et al. Circulating breast tumor cells exhibit dynamic changes in epithelial and mesenchymal composition. *Science* 2013; 339(6119): 580-4.
36. Chan C M, Au T C, Chan A T, et al. Advanced technologies for studying circulating tumor cells at the protein level. *Expert Rev Proteomics* 2013; 10(6):579-89.
37. Scatena R, Bottoni P, Giardina B. Circulating tumour cells and cancer stem cells: a role for proteomics in defining the interrelationships between function, phenotype and differentiation with potential clinical applications. *Biochim Biophys Acta* 2013; 1835(2):129-43.
38. Leman E S, Getzenberg R H. Nuclear structure as a source of cancer specific biomarkers. *J Cell Biochem* 2008; 104(6):1988-93.
39. Veltri R W, Christudass C S, Isharwal S. Nuclear morphometry, nucleomics and prostate cancer progression. *Asian J Androl* 2012; 14(3):375-84.
40. Coumans F A, Doggen C J, Attard G, et al. All circulating EpCAM+CK+CD45− objects predict overall survival in castration-resistant prostate cancer. *Ann Oncol* 2010; 21(9):1851-7.
41. Coumans F A, van Dalum G, Beck M, et al. Filter characteristics influencing circulating tumor cell enrichment from whole blood. *PLoS One* 2013; 8(4):e61770.
42. Goodman O B, Jr., Symanowski J T, Loudyi A, et al. Circulating tumor cells as a predictive biomarker in patients with hormone-sensitive prostate cancer. *Clin Genitourin Cancer* 2011; 9(1):31-8.
43. Resel Folkersma L, Olivier Gomez C, San Jose Manso L, et al. Immunomagnetic quantification of circulating tumoral cells in patients with prostate cancer: clinical and pathological correlation. *Arch Esp Urol* 2010; 63(1):23-31.
44. Amato R J, Melnikova V, Zhang Y, et al. Epithelial cell adhesion molecule-positive circulating tumor cells as predictive biomarker in patients with prostate cancer. *Urology* 2013; 81(6):1303-7.
45. Sweeney C, Chen Y H, Carducci M A, et al. Impact on overall survival (OS) with chemohormonal therapy versus hormonal therapy for hormone-sensitive newly metastatic prostate cancer (mPrCa): An ECOG-led phase III randomized trial. *J Clin Oncol* 32:5s, 2014 (suppl; abstr LBA2).

Example 2: Sub-Classification of Prostate Cancer Circulating Tumor Cells (CTCs) by Nuclear Size Reveals Very-Small Nuclear CTCs in Patients with Visceral Metastases While enumeration of circulating tumor cells (CTCs) has shown some clinical value, the pool of CTCs contains a mixture of cells which contains additional information that can be extracted. Our group sub-classified CTCs by shape features focusing on nuclear size and related this to clinical information.

A total of 148 blood samples were obtained from 57 Pancreatic Cancer (PC) patients across the spectrum of metastatic states: no metastasis, non-visceral metastasis, and visceral metastasis. CTCs captured and enumerated on NanoVelcro Chips were subjected to pathologic review including nuclear size. The distribution of nuclear sizes was analyzed using a Gaussian Mixture Model. Correlations were made between CTC subpopulations and metastatic status.

Statistical modeling of nuclear size distribution revealed 3 distinct subpopulations: large-nuclear (lnCTC), small-nuclear (snCTC), and very-small-nuclear CTCs (vsnCTCs). snCTC+vsnCTC identified patients with metastatic disease. vsnCTC counts alone, however, were elevated in patients with visceral metastases when compared to those without (0.36±0.69 vs. 1.95±3.77 cells/mL blood, p<0.001). Serial enumerations suggested the emergence of vsnCTCs occurred prior to the detection of visceral metastases.

There are morphologic subsets of CTCs that can be identified by fundamental pathologic approaches, such as nuclear size measurement. This observational study strongly suggests that they contain relevant information on disease status. In particular, the detection of vsnCTCs correlated with the presence of visceral metastases and should be formally explored as a putative blood-borne biomarker to identify patients at risk for developing this clinical evolution of PC.

Introduction

Prostate cancer (PC) remains an important public health problem as almost 30,000 are expected to die of this disease in 2014.[1] Within the group of men at risk for death from this disease, there is range of clinical behaviors including progression to visceral metastases, which spread to non-osseous, non-nodal sites including the liver and/or lungs.[2-4] It is recognized that men with visceral metastases have significantly shorter survival in comparison to those who do not progress in this fashion[5]. These progression events often lead to organ failure followed shortly by death. In typical practice, patients are monitored by serum PSA concentration without frequent radiographic assessment. It is recognized, however, that serum PSA changes do not detect[6-8] certain disease alterations such as emergence of non-PSA producing neuroendocrine PC (NEPC) or small cell PC. Moreover, PSA monitoring provides little insight into other clinical alterations which have prognostic importance such as the development of visceral metastases. By the time these lesions are detected radiographically or clinically (by altered organ function), the metastatic lesions have been present for some time. Additional highly-sensitive, minimally-invasive, serially-obtainable means of monitoring disease status are still needed, especially for the visceral progression events.

Circulating tumor cells (CTCs) have arisen as contemporary prognostic and predictive biomarkers for PC.[9] Their value has been demonstrated mainly in enumeration.[10-17] The conventional, FDA-approved CTC assay has not been useful in measuring certain changes in clinical behavior such as the detection of emerging or occult visceral spread.[13] CTCs are a heterogeneous population.[18, 19] We and others have proposed that subclassification of these cells could augment their clinical utility.[20-22] To this end, morphologic classification has always been a fundamental practice in pathology. While Gleason grading has been highly informative, nuclear size and shape in tumor sections have also been shown to correlate with distant metastasis and death in PC.[23-25] These morphologic alterations have been associated with changes in signaling pathways that drive various pro-tumorigenic and pro-metastatic processes through a structure-function relationship.[26] Since biological alterations, which affect the natural history of disease, cause structural alteration in cells (including the pool of CTCs), we hypothesized that variations in the CTC morphology and nuclear size can be used to detect the changes in disease phenotype such as the detection and possibly prediction of visceral metastases.

In this example, we acquired blood specimens from PC patients across a broad spectrum of metastatic states: no metastasis, non-visceral (osseous and/or nodal) metastasis, and visceral (hepatic and/or pulmonary) metastasis. We isolated and enumerated CTCs using NanoVelcro Chips[27, 28], an emerging CTC isolation system that utilizes a combination of a microfluidic chaotic mixer and a nanostructured capture substrate that functions with high sensitivity. By incorporating higher-resolution fluorescence microscopy into the NanoVelcro system, we were able to visualize cellular features of the captured CTCs (DAPI+/CK+/CD45-) and perform pathologic review for cellular morphology and nuclear size. This led to the identification of nuclear size-defined CTC subsets. Our study showed that these subsets correspond to metastatic state.

Figure 8:
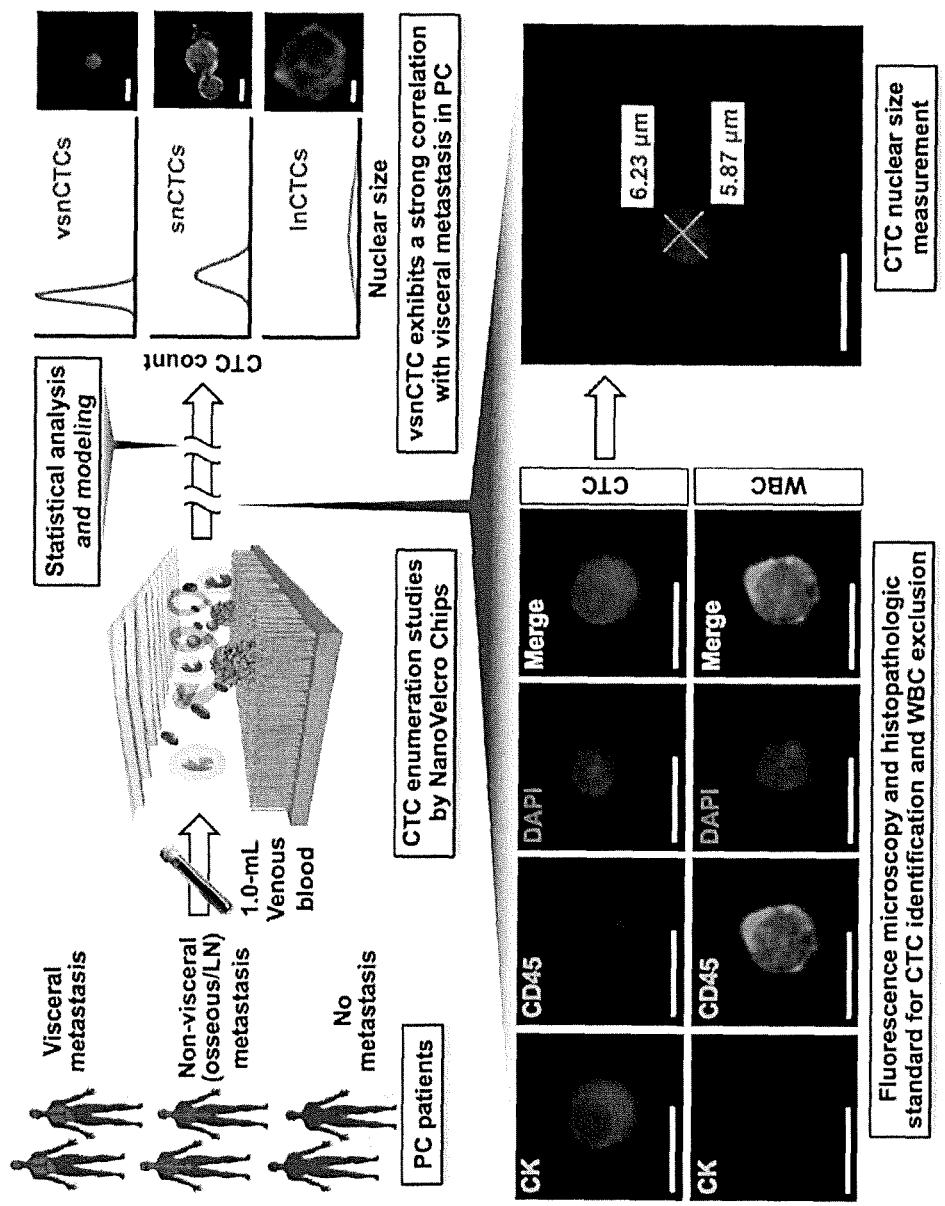
FIG. 8 shows a schematic of the study design for identifying very-small-nuclear CTCs (vsnCTCs).

FIG. 8 shows a schematic of the study design for identifying very-small-nuclear CTCs (vsnCTCs). PC patients were recruited for CTC enumeration studies and each sample was placed into one of three cohorts depending on the metastatic status of the patient at the time of collection including: visceral metastasis, non-visceral (osseous/lymph node) metastasis, and non-metastatic disease. CTC enumeration studies were performed using highly sensitive NanoVelcro Chips in conjunction with the use of fluorescence microscopy. The identified CTCs (DAPI+/CK+/CD45-) were then subjected to nuclear size measurements. Through biostatistical analysis and modeling, we identified three subpopulations of CTCs: large-nuclear CTCs (lnCTCs), small-nuclear CTCs (snCTCs) and very-small-nuclear CTCs (vsnCTCs). The emergence of vsnCTCs correlates with the onset or presence of visceral metastases and may serve as the basis for a new diagnostic assay targeting the most aggressive form of PC. (Scale bars in the figures indicate 10 μm)

Patients and Methods

Patients and Samples

Blood specimens for this study were extracted from existing biobanking protocols approved by the Cedars-Sinai Medical Center (CSMC) Institutional Review Board (IRB). The entire pool of patients consisted of men with histologically confirmed PC agreeing to provide blood as part of CSMC biobanking protocols who underwent evaluation and/or treatment at CSMC between January 2013 and December 2014. Use of all biospecimens from the banking studies was also conducted under IRB oversight. As such, this study was conducted as an observational study to determine the range and distributions of CTC nuclear sizes in a single institution cohort of men with PC. Radiographic evaluation within 3 months of sample collection was required for inclusion in this analysis. Multiple blood draws from individual patients were allowed. Patients and their enumeration studies were classified by sites of metastasis into one of three categories: no metastases, non-visceral metastases, or visceral metastases, according to the contemporary radiographic evidence. Samples and patients categorized as "non-visceral metastases" indicated that the subject had osseous lesions and/or lymph node spread on most recent radiographic studies. Samples and patients categorized as "visceral metastases" indicated that the subject had radiographically detected lesions in soft tissue organs such as the liver or lungs with or without bone or lymph node involvement on recent imaging. We conducted a statistical analysis and modeling of CTC nuclear size distribution to sub-classify CTCs. Correlations were made between CTC subpopulations and metastatic status (see Statistical analysis below).

CTC Enrichment Using NanoVelcro Chips

Figure 9:
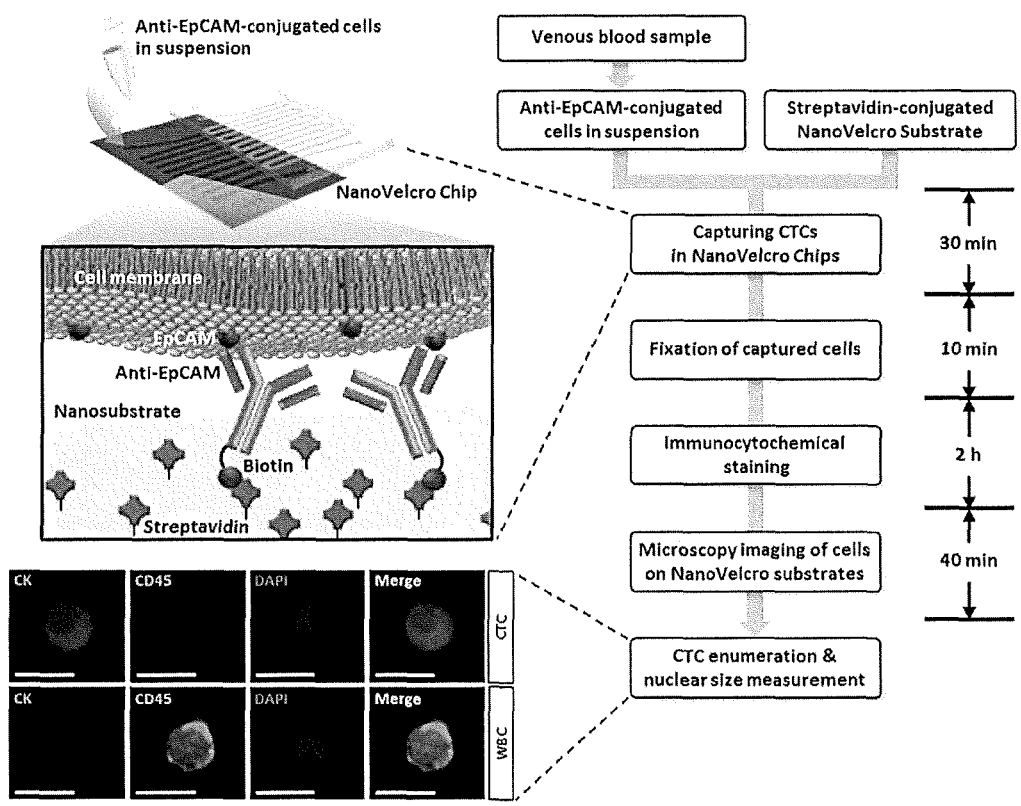
FIG. 9 shows a schematic of the general protocol for CTC enrichment by NanoVelcro Chips.

The general protocol for CTC enrichment by NanoVelcro Chips is summarized in a workflow as shown in FIG. 9. FIG. 9 shows a schematic of the general protocol for CTC enrichment by NanoVelcro Chips. Red blood cells were depleted from the collected venous blood and the remaining cells were incubated with biotinylated goat anti-human EpCAM. After washing carefully, the sample was loaded into the NanoVelcro Chip. The cell suspension was introduced into the chip by an automated fluid handler at a consistent flow rate. The CTCs were captured on the NanoVelcro substrate while the sample flows through the microfluidic channels during this 30-minute step. After fixation by paraformaldehyde, the cells immobilized on the nanosubstrate were subjected to immunocytochemical staining with DAPI, rabbit anti-pan-cytokeratin, mouse anti-CD45, Alexa Fluor 488-conjugated anti-rabbit, and Alexa Fluor 555-conjugated anti-mouse. CTCs were identified as DAPI+/CK+/CD45− objects that passed standard pathologic review to ensure their morphology consistent with an epithelial cell and not a hematologic cell. The CTC count of each chip was recorded and the nuclear sizes of the CTCs were measured along the longest axis and the width perpendicular to that axis.

Venous blood was collected in acid-citrate dextrose-containing vacutainers (BD Bioscience, San Jose, Calif., USA) and processed within 4 hours of collection. CTCs were isolated using NanoVelcro Chips as previously described.[27,28] In brief, 1.0 mL of venous blood was subjected to red blood cell (RBC) depletion using a standard RBC lysis buffer (containing $NH_4Cl$ and Tris, pH 7.2). The remaining cells were incubated with a capture agent (biotinylated goat anti-human EpCAM antibody, R&D Systems). After washing carefully, the sample was loaded into the NanoVelcro Chip, which consists of a streptavidin-coated NanoVelcro substrate and an overlaid polydimethylsiloxane (PDMS) chaotic mixer. In conjunction with the use of an automated fluid handler, the cell suspension was introduced into the chip at a consistent flow rate (0.5 mL/h). After fixation using 2% paraformaldehyde (PFA, Electron Microscopy Science), the cells immobilized on the NanoVelcro substrate were subjected to immunocytochemical (ICC) staining with DAPI (Vector Laboratories, Burlingame, Calif., USA), rabbit anti-pan-cytokeratin (Life technologies, Grand Island, N.Y., USA, and Abcam, Cambridge, Mass., USA), mouse anti-CD45 (BD Biosciences, San Jose, Calif., USA, and Abcam, Cambridge, Mass., USA), Alexa Fluor 488-conjugated anti-rabbit, and Alexa Fluor 555-conjugated anti-mouse (Life technologies, Grand Island, N.Y., USA). Subsequent microscopic imaging was performed to identify the CTCs. For selected cases, chicken anti-synaptophysin (Abcam, Cambridge, Mass., USA) and Alexa Fluor 647-conjugated anti-chicken (Life technologies, Grand Island, N.Y., USA) were used.

CTC Imaging Followed by Nuclear Size Measurements

NanoVelcro Chips were imaged using an upright fluorescence microscope (Eclipse 90i, Nikon) with NIS-Element imaging software (Nikon). An automatic scan over the NanoVelcro chip was carried out by the imaging system under 40× magnification with DAPI, FITC and TRITC channels corresponding to nuclear, CK, and CD45 staining respectively. The DAPI+/CK+/CD45− events (FIG. 8) were selected as candidate CTCs and were further subjected to another scan at either 100× or 400× magnification. All high-resolution images were reviewed by a pathologist to ensure that CTC calls were morphologically consistent with an epithelial cell and not a hematologic cell.

Nuclear size of all identified CTCs was measured along the longest axis and the width perpendicular to that axis (FIG. 8).[29,30] The nuclear size for statistical analyses is defined as follows:

$$\text{nuclear size} = \sqrt{(\text{longest axis}) \times (\text{perpendicular width})}$$

To ensure the consistency and accuracy of nuclear size measurements on NanoVelcro Chips, we performed a series of calibration studies using PC cell lines and blood samples from PC patients.

Figures 10A, 10B, 10C, 10D:
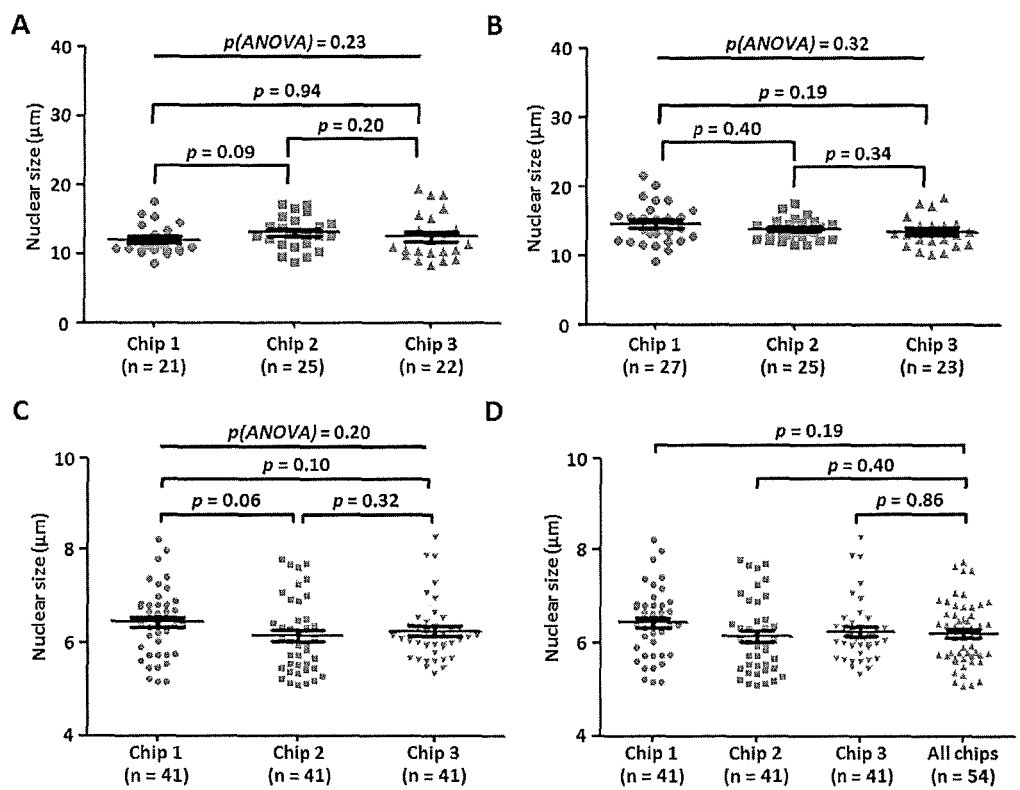
FIGS. 10A-10D show data graphs showing the reproducibility of nuclear size measurement on NanoVelcro Chips.

FIGS. 10A-10D show data graphs showing the reproducibility of nuclear size measurement on NanoVelcro Chips. Cell line studies and randomly selected enumeration tests for patient samples were used to validate the reproducibility of nuclear size measurement on NanoVelcro Chips. FIG. 10A shows nuclear size measurement for PC3 cells on NanoVelcro substrates showed no significant difference among the three or between any two repeats of PC3 cell studies. Similar results were demonstrated by LNCaP cell studies, as shown in FIG. 10B. We also randomly sampled three enumeration tests from the 148 ones performed for the PC patients. From each of the selected NanoVelcro Chip we identified 40 small lymphocytes based on histopathological and immunocytochemical criteria (CD45+/CK−/DAPI+), and measured their nuclear size. No significant difference was found among the three or between any two randomly sampled enumeration tests, as shown in FIG. 10C. Moreover, we also randomly picked 54 small lymphocytes across the 148 enumeration tests and measured their nuclear sizes. As demonstrated in FIG. 10D, the mean of these cross-test-sampled 54 small lymphocytes was not significantly different from any of the three tests measuring small lymphocytes. All the p values were indicated in the figures.

Statistical Analyses

To identify the subpopulations of CTCs, we performed a cluster analysis for the CTC nuclear sizes using the Gaussian Mixture Model (GMM) formed by K Gaussian components with varied variances. The means and variances of K Gaussian components were estimated by the Expectation-Maximization (EM) algorithm[31] and the optimal number K was decided by the Akaike information criterion (AIC)[32] and Bayesian information criterion (BIC)[33]. Based on its nuclear size, each CTC was assigned to a cluster with the maximum likelihood of all K Gaussian components. $\chi^2$ test was performed to test the independency of our unsupervised clustering of CTCs on metastatic categories.

Since metastatic status was subject to change over the disease course, the correlational analyses in this study were based on enumeration studies instead of the patients, and multiple enumeration studies from serial time points are allowed. Wilcoxon rank-sum tests were used to evaluate the statistical differences of the CTC counts of the enumeration studies between different metastatic categories: 1) metastasis versus no metastasis and 2) non-visceral metastasis versus visceral metastasis. Considering the potentially independent nature of multiple blood samples and enumeration studies from the same patients, we further adopted a Poisson generalized linear mixed model (GLMM) to test the correlation between metastatic status and CTC counts adjusted for the potential effect resulting from repeated measurements.

The statistical tests in this study were performed using the R statistical software version 3.1.1 (http://www.r-project.org/). The GLMM analysis was performed using package glmmML version 1.0.[34] All the tests are two-sided and p values less than 0.05 were considered statistically significant.

Results

Patient Characteristics and Sample Collections for CTC Enumeration Studies

Blood samples from a total of 57 PC patients comprised the full complement of subjects utilized in this analysis. Detailed clinical characteristics of the patients are summarized in Table 1. The classification of the patient and their enumeration studies based on their sites of metastasis is also listed. Each patient had between 1 and 11 enumeration studies performed yielding a total of 148 enumeration studies (enumeration studies from each patient are listed in Table 2).

TABLE 1

Patent Characteristics

| Patient classification | Patients (n = 57)[a] | Enumeration Samples (n = 148)[a] | Metastatic status |
|---|---|---|---|
| Patients undergoing local therapy | 14 | 15 | No metastases |
| Patients on surveillance after local therapy | 4 | 5 | No metastases |
| Patient who developed recurrence after local disease Castration Sensitive | | | |
| No metastatic disease (PSA only) | 3 | 3 | No metastases |
| Known metastatic disease | | | |
| Bone/LN metastases only | 4 | 6 | Nonvisceral (osseous/LN) metastases |
| Bone/LN and visceral metastases | 0 | 0 | visceral metastases |
| Castration resistant | | | |
| No metastatic disease (PSA only) | 3 | 8 | no metastases |
| Known metastatic disease | | | |
| Bone/LN metastases only | 17[a] | 38[a] | Nonvisceral (osseous/LN) metastases |
| Bone/LN and visceral metastases | 13[a] | 61[a] | visceral metastases |
| Visceral metastases only[b] | 2[b] | 12[b] | visceral metastases |

Abbreviations: LN, lymph node; PSA, prostate-specific antigen

[a] Patients with changes in their metastatic status during follow-up were placed in all the categories to which they belonged or had belonged. However, the change in status was reflected in the categorization of enumeration studies

[b] Patients and enumeration studies were included in the correlation analysis for metastasis but not in the analysis for visceral metastasis due to the absence of coexisting non visceral metastasis.

TABLE 2

Enumeration studies, Patients who contributed the enumeration studies, and excluded enumeration studies.

| Patient | Enumeration studies | Patient | Enumeration studies | Patient | Enumeration studies |
|---|---|---|---|---|---|
| No metastasis | | | | | |
| 392 | □ | 463 | □ | 3501 | □ |
| 450 | □ | 464 | □ | 3502 | □ |
| 453 | □ | 465 | □ | 3702 | □ |
| 454 | □ | 467 | □ | 3801 | □ □ |
| 457 | □ | 1159 | □ □ | 3803 | □ |
| 459 | □ | 1347 | □ □ □ □ | 3810 | □ |
| 461 | □ | 3301 | □ | 3903 | □ |
| 462 | □ | 3401 | □ | 31001 | □ |
| Non-Visceral (osseous and/or nodal) metastasis | | | | | |
| 1117 * | □ □ □ □ | 1308 | □ □ □ □ □ □ | 3712 | □ |
| 1161 * | □ □ □ | 1336 | □ □ □ | 3714 | □ □ |
| 3701 * | □ □ | 1314 | □ □ | 3715 | □ |
| 446 | □ | 1365 | □ □ | 3802 | □ □ □ |
| 1165 | □ | 3703 | □ □ | 3805 | □ |
| 1185 | □ | 3707 | □ | 3808 | □ |
| 1268 | □ | 3708 | □ □ □ | 3901 | □ □ |
| Visceral (hepatic and/or pulmonary) metastasis | | | | | |
| 1117 * | □ □ | 3704/002 | □ □ □ □ □ □ | 012 | □ □ □ □ □ □ □ |
| 1161 * | □ | 1350/004 | □ □ □ □ | 014 | □ □ □ □ □ □ □ □ |
| 3701 * | □ □ | 1367/006 | □ □ □ □ □ □ | 3804 | □ □ |
| 1366 | □ □ | 010 | □ □ □ □ □ □ | 390 † | ▨ |
| 1354 | □ □ | 011 | □ □ □ □ □ □ | 3701/009 † | ▨ ▨ ▨ ▨ ▨ ▨ ▨ ▨ ▨ ▨ |

□ Enumeration studies included in the correlational analyses (FIGS. 13A-13C and FIGS. 15A-15C).

▨ Enumeration studies included in the correlational analyses for metastasis (FIGS. 13A-13C) but not included in the analysis for visceral metastasis (FIGS. 15A-15C) due to the absence of co-existing non-visceral metastasis.

* Patients who changed the metastatic status during the time of following up were placed in all the categories they belonged or had belonged to. However the change in diagnosis is reflected in the categorization of enumeration studies.

† Patients included in the correlational analyses for metastasis (FIGS. 13A-13C) but not included in the analysis for visceral metastasis (FIGS. 15A-15C) due to the absence of co-existing non-visceral metastasis.

Figures 11A, 11B:
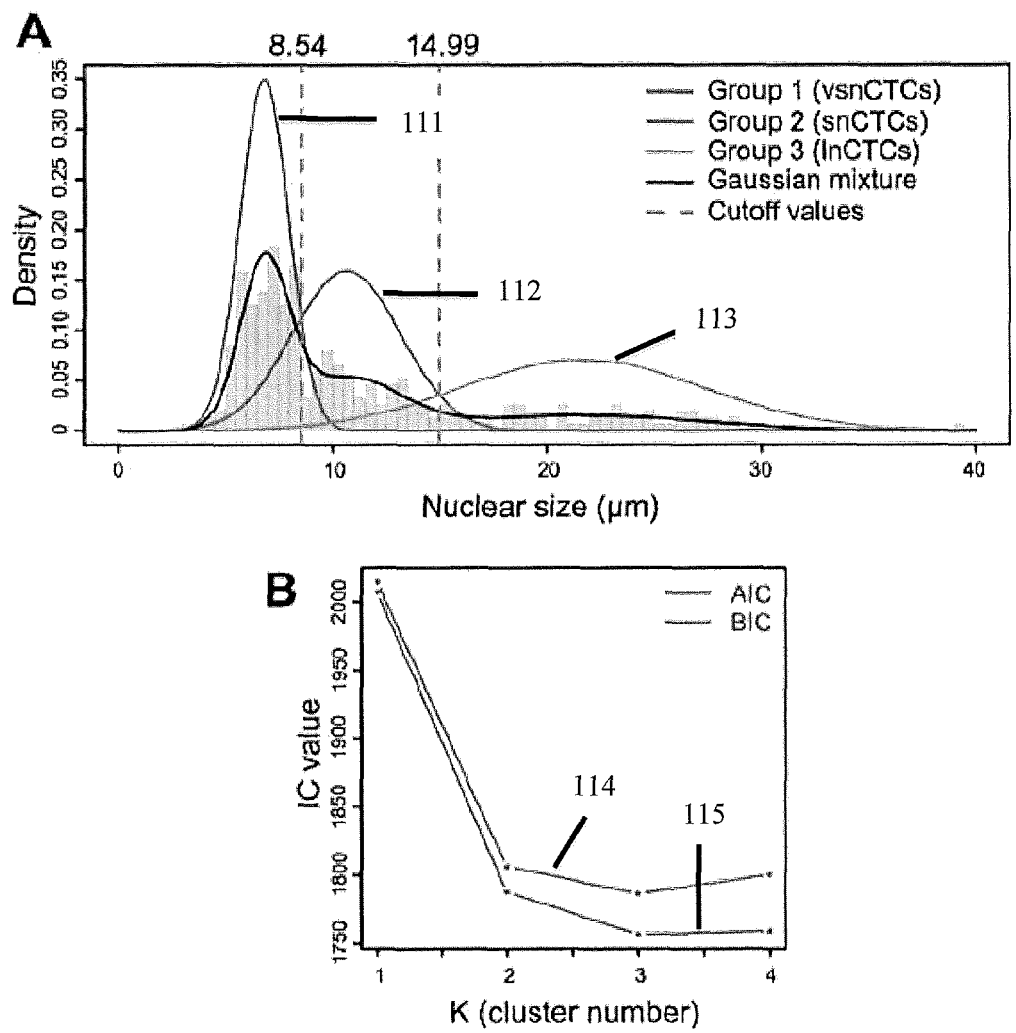
FIGS. 11A-11B show data graphs demonstrating results for statistical analysis and modeling of CTC nuclear size distribution and CTC subpopulations.

Statistical Analysis and Modeling of CTC Nuclear Size Distribution and CTC Subpopulations The CTC data pool was generated by performing 148 enumeration studies (as serial collections were used) that provided a total of 304 CTCs for analyzing the nuclear size distribution. FIGS. 11A-11B show data graphs demonstrating results for statistical analysis and modeling of CTC nuclear size distribution and CTC subpopulations. FIG. 11A shows a histogram depicting the distribution of 304 CTCs according to their nuclear sizes. The black solid line shows the density of the optimal Gaussian mixture model (GMM) that best fits the histogram. Lines 111, 112, and 113 represent the three cluster-specific Gaussian density curves (Groups 1, 2 and 3, respectively). The dash lines indicate the cutoffs of our classification rule: assigning a sample to the cluster with the maximum Gaussian likelihood. In FIG. 11B, line 115 shows the AIC values and line 114 shows the BIC values for K (cluster number) from 1 to 4. The best cluster number is 3 as both AIC and BIC reached the minimum when K=3.

Based on the AIC and BIC, the optimal model was determined to be a 3-cluster GMM with cluster means at 6.82, 10.63, 21.63 µm, and standard deviations of 1.14, 2.51, 5.67 µm (FIG. 11A). The AIC and BIC values of different cluster numbers are also shown (FIG. 11B). We then assigned CTCs into the cluster with the maximum Gaussian likelihood, and yielded three CTC subpopulations that we labeled as very-small-nuclear CTCs (vsnCTCs, nuclear size <8.54 µm), small-nuclear CTCs (snCTCs, nuclear size between 8.54 µm and 14.99 µm) and large-nuclear CTCs (lnCTCs, nuclear size >14.99 µm).

Relationship Between CTC Nuclear Sizes and Metastatic Status

Figures 12A, 12B, 12C, 12D:
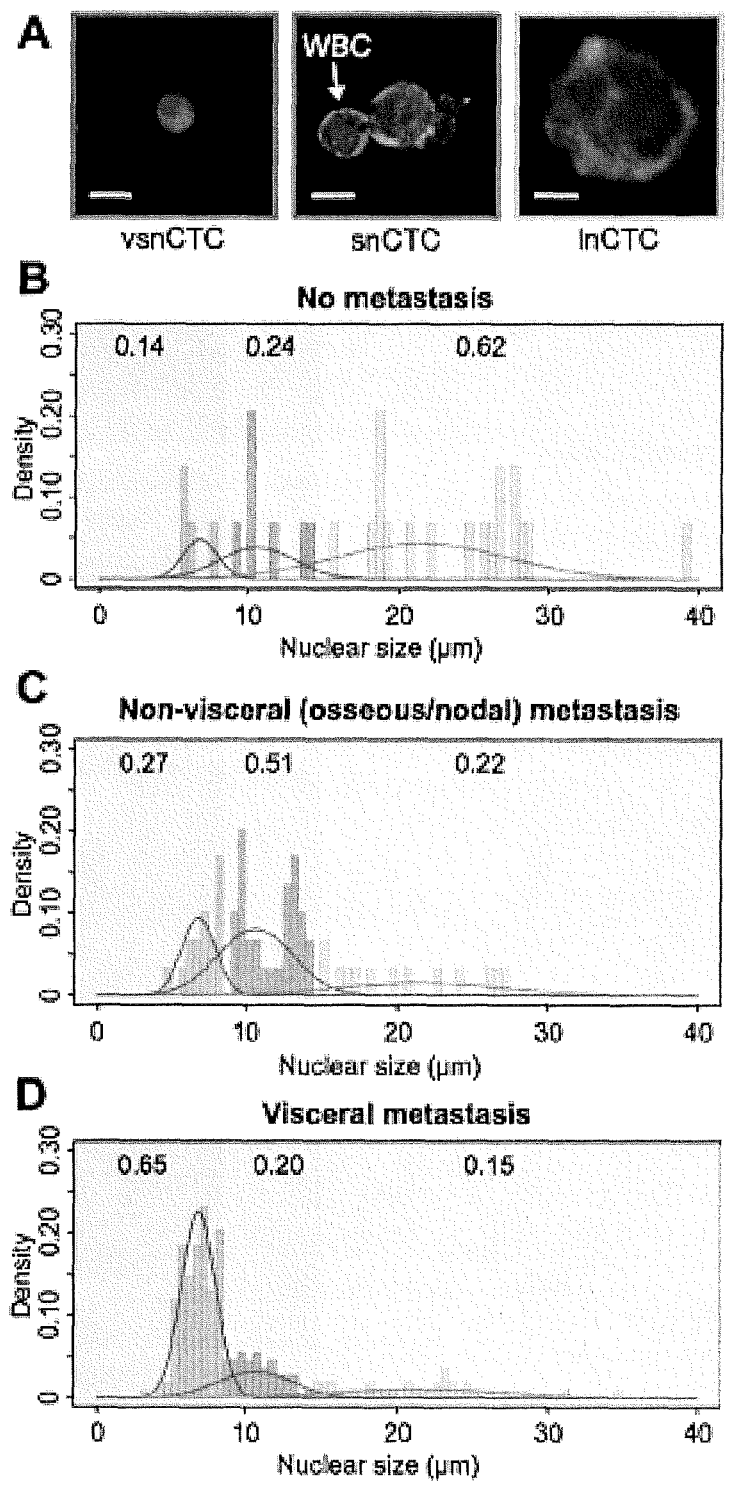
FIGS. 12A-12D show fluorescent microscopy images of CTCs and data graphs showing the relationship between CTC nuclear sizes and metastatic status.

To further analyze the relationship between the three CTC subpopulations and metastatic status, histograms were plotted using density of CTC counts versus nuclear sizes for each metastatic status category (FIGS. 12A-12D). FIGS. 12A-12D show fluorescent microscopy images of CTCs and data graphs showing the relationship between CTC nuclear sizes and metastatic status. FIG. 12A shows representative images of a lnCTC, a snCTC and a vsnCTC taken by fluorescence microscopy. The cells are stained with DAPI, Alexa Fluor 488-conjugated anti-CK, and Alexa Fluor 555-conjugated anti-CD45. Histograms and cluster-specific Gaussian density curves were plotted using CTC counts versus nuclear sizes and classified into three metastatic statuses: FIG. 12B shows no metastasis, in which lnCTCs account for the largest proportion (62%) among all the CTCs; FIG. 12C shows non-visceral metastasis, in which snCTCs constitute the major subpopulation (51%), followed by vsnCTCs (27%); and FIG. 12D shows visceral metastasis, in which vsnCTCs account for the largest proportion of cells (65%), followed by snCTCs (20%). The proportions of the three CTC subpopulations varied significantly between different metastatic statuses as demonstrated by a two-sided $\chi^2$ test (p=$2.29 \times 10^{-13}$).

The proportions of the three CTC nuclear subtypes (examples in FIG. 12A) varied significantly between the different metastatic categories. In the cohort of non-metastatic patients (FIG. 12B), the majority of cells were classified as lnCTCs (62%). In the category of non-visceral metastasis (FIG. 12C), the snCTCs constituted the major CTC subpopulation (51%), followed by vsnCTCs (27%). In the category of visceral metastasis (FIG. 12D), the vsnCTCs constituted the major CTC subpopulation (65%), followed by snCTCs (20%). This result shows that our unsupervised clustering of CTCs has significant dependency on metastatic categories (two sided $\chi^2$ test, p=$2.29 \times 10^{-13}$, Table 3).

TABLE 3

Proportions of CTC subpopulations in different metastatic status

|  |  | Counts of CTC subpopulations | | |
| --- | --- | --- | --- | --- |
|  |  | vsnCTC | snCTC | lnCTC |
| Metastasis status | No metastasis | 4 | 7 | 18 |
|  | Non-visceral (osseous/LN) metastasis | 16 | 30 | 13 |
|  | Visceral metastasis | 140 | 43 | 33 | snCTC+vsnCTC Counts Correlate with Metastasis

Figures 13A, 13B, 13C:
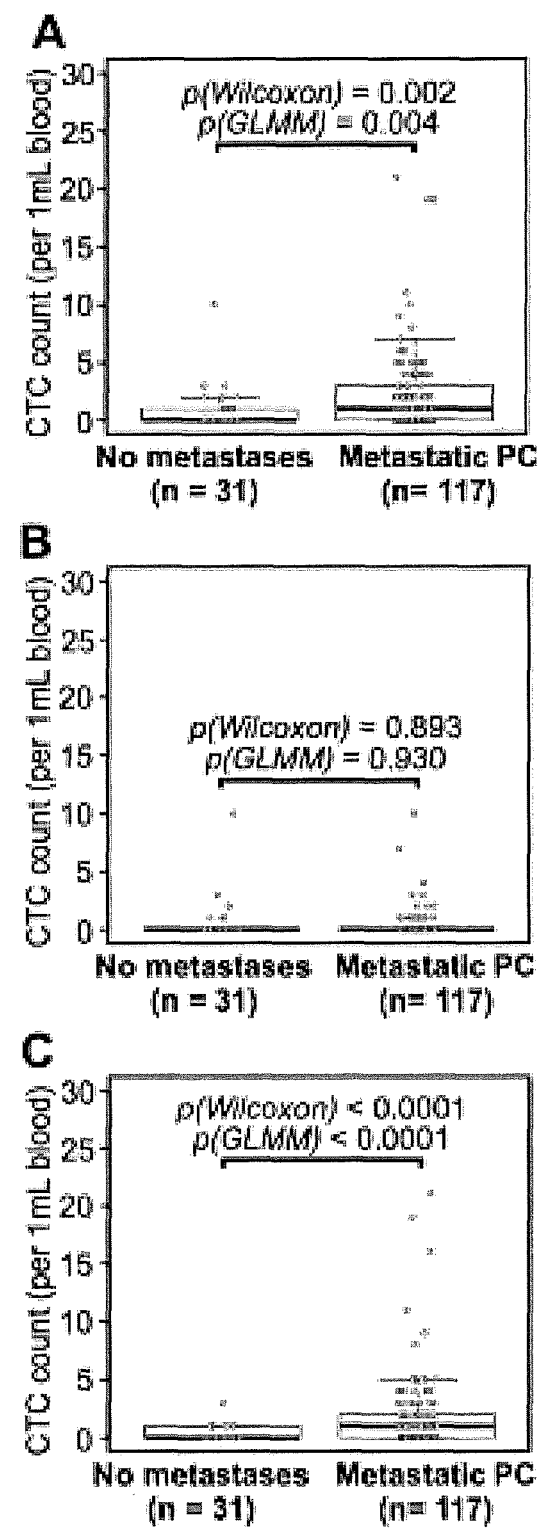
FIGS. 13A-13C show graphs demonstrating the correlation between snCTC+vsnCTC counts and metastatic PC.
Figure 14:
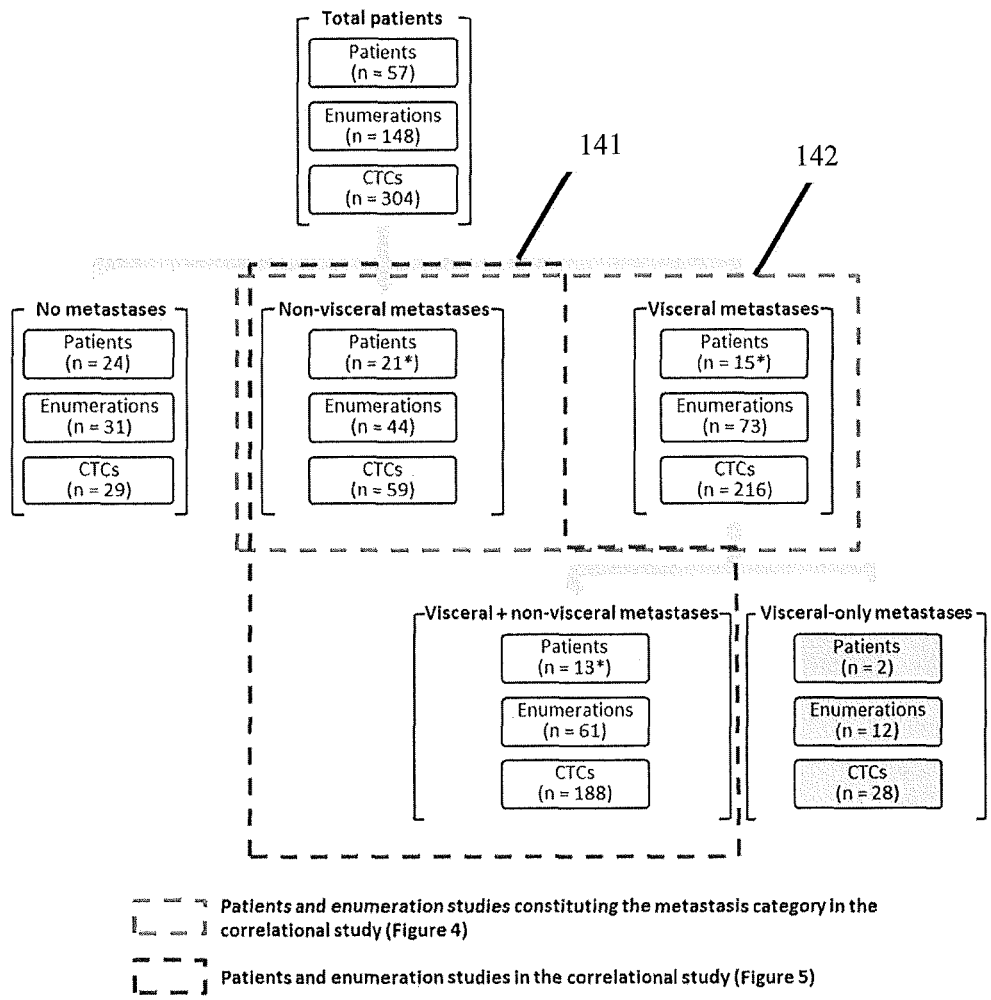
FIG. 14 is a schematic of patients and enumeration studies for correlational analyses.

We then performed a statistical analysis on the 148 enumeration studies to measure the correlation between CTC subpopulations and metastatic state. The pool consisted of 31 enumeration studies in the no metastasis category, and 117 in the metastatic PC category (combination of non-visceral metastasis and visceral metastasis categories). FIGS. 13A-13C shows graphs demonstrating the correlation between snCTC+vsnCTC counts and metastatic PC. Box plots are shown for FIG. 13A) total CTC counts, FIG. 13B) lnCTC counts, and FIG. 13C) snCTC+vsnCTC counts in 1.0 mL of blood. Boxes represent interquartile range, and the horizontal line across each box indicates median value. The y-axis represents CTC counts per 1.0 mL of blood. There are 31 enumerations from the category of no metastasis and 117 from metastatic PC patients (FIG. 14). FIG. 14 is a schematic of patients and enumeration studies for correlational analyses. Among the patients we recruited, there is a spectrum of clinical behaviors (see Table 1). For our correlational analyses in FIGS. 13A-13C, we included all the enumeration studies from the patients with metastatic PC (dot line box 142, non-visceral and visceral metastasis) to form the sample pool of metastasis category. This provided a total of 117 enumeration studies in the analysis between CTC subsets and metastasis in PC. For the analysis in FIGS. 15A-15C, we examined the correlation between CTC subsets and visceral metastases in PC. We only included the enumeration studies from the patients with non-visceral metastases and those with co-existing visceral metastases and non-visceral metastases (dot line box 141).

The data showed that the snCTC+vsnCTC counts obtained by using these nuclear size-based CTC definitions provide more information on metastatic status in PC than total CTC count. Statistical analyses were performed using two-sided Wilcoxon tests and Wald tests following a Generalized Linear Mixed Model (GLMM). All the p values are indicated in the figures.

When examining the total CTC count (lnCTC+snCTC+vsnCTC), there was a statistically significant difference between metastatic and non-metastatic disease (0.94±1.91 versus 2.42±3.60 cells per mL of blood, p=0.002, FIG. 13A). In an additional interrogation, the lnCTC subpopulation alone failed to distinguish metastatic and non-metastatic disease (0.58±1.88 versus 0.40±1.28 cells per mL of blood, p=0.893, FIG. 13B). snCTC+vsnCTC counts, in contrast, remained significantly different (0.35±0.66 versus 2.02±3.36 cells per mL of blood, p<0.0001, FIG. 13C). To assess the potential effect resulting from repeated measurements from the same patients, analysis using GLMM was conducted to test the correlation between metastatic status and CTC counts. The p values obtained using GLMM were consistent with those from the Wilcoxon tests (indicated in figures). These data were consistent with the preferential distribution of snCTCs and vsnCTCs in FIG. 12C and FIG.

12D, and demonstrated the benefit of categorization of CTCs by nuclear size (<14.99 μm). Overall, the snCTC+ vsnCTC counts obtained by using these CTC definitions provided more information on metastatic status in PC than total CTC count.

vsnCTC Counts Correlate with the Presence of Visceral Metastasis

We further investigated the correlation between CTC subsets and visceral metastasis. These analyses were performed using 105 enumeration studies from patients who had radiographically detectable osseous and/or nodal lesions, with or without visceral organ involvement. Among these enumeration studies, 44 were in the non-visceral metastases category and 61 were in the visceral metastases category (FIG. 14).

Figures 15A, 15B, 15C:
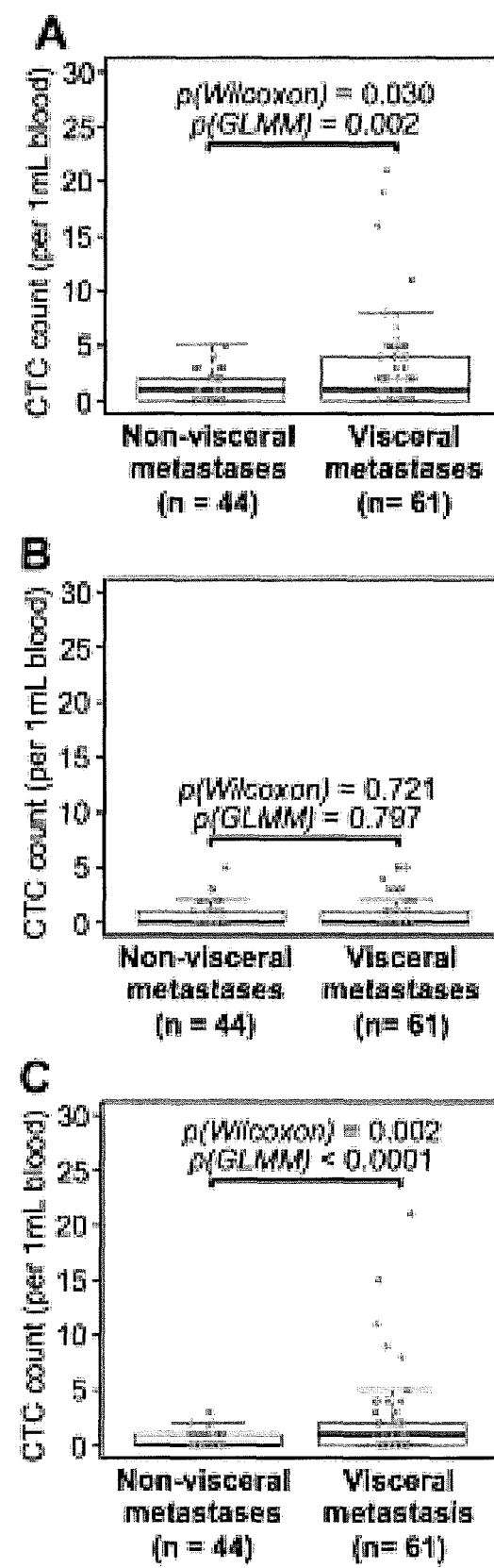
FIGS. 15A-15C show graphs displaying the correlation between vsnCTC counts and aggressive PC with visceral metastasis.

FIGS. 15A-15C shows graphs displaying the correlation between vsnCTC counts and aggressive PC with visceral metastasis. Box plots are shown for FIG. 15A) snCTC+ vsnCTC counts, FIG. 15B) snCTC counts, and FIG. 15C) vsnCTC counts in 1.0 mL of blood. Boxes represent interquartile range, and the horizontal line across each box indicates median value. The y-axis represents CTC counts per 1.0 mL of blood. There are 44 enumerations from the category of non-visceral metastasis and 61 from the category of visceral metastasis. The results indicated that vsnCTCs rather than snCTCs are correlated with the presence of visceral metastases. Statistical analyses were performed using two-sided Wilcoxon tests and Wald tests following a Generalized Linear Mixed Model (GLMM). All the p values are indicated in the figures.

We found that snCTC+vsnCTC counts differed significantly between non-visceral metastasis and visceral metastasis categories ($1.05 \pm 1.26$ versus $2.69 \pm 4.27$ cells per mL of blood, $p=0.030$, FIG. 15A). Recognizing the preferential distribution of snCTCs and vsnCTCs in FIG. 12C and FIG. 12D, we pursued further statistical analyses of individual CTC subpopulations. Alone, snCTC counts were unable to distinguish metastatic subpopulations ($0.68 \pm 1.12$ versus $0.74 \pm 1.38$ cells per mL of blood, $p=0.721$, FIG. 15B). In contrast, vsnCTC counts successfully distinguished visceral metastatic from non-visceral-metastatic PC patients ($0.36 \pm 0.69$ versus $1.95 \pm 3.77$ cells per mL of blood, $p=0.002$, FIG. 15C). The p values obtained using GLMM and were consistent with those from the Wilcoxon tests (indicated in figures). These data combined with the distribution of vsnCTCs in FIG. 12D indicated that vsnCTCs rather than snCTCs are correlated with the presence of aggressive PC with visceral involvement.

Summary of Clinical Cases with Visceral Metastases

Figure 16:
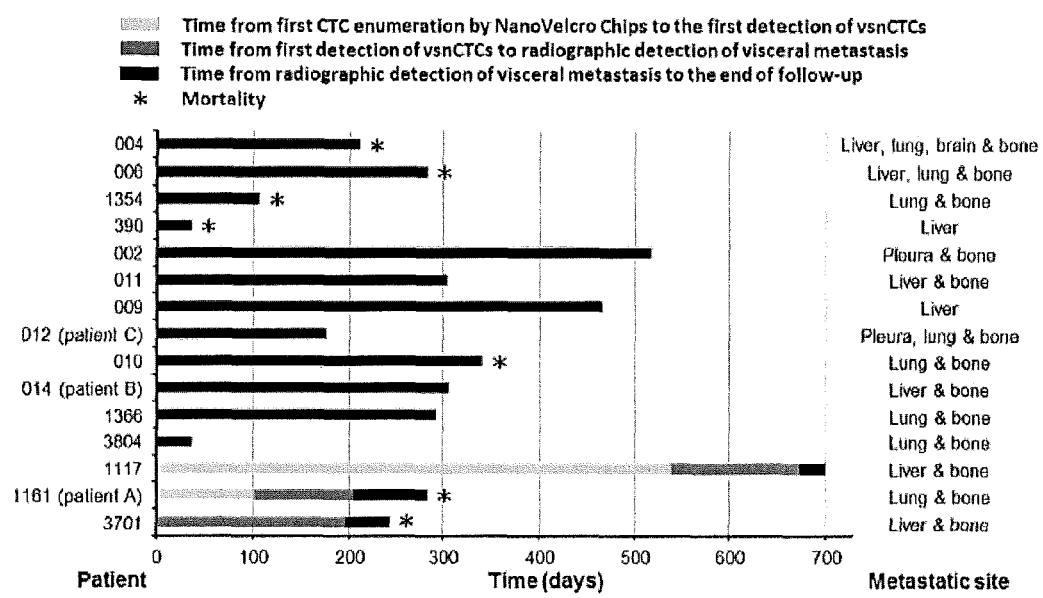
FIG. 16 shows a graph summarizing the 15 patients with visceral metastases.

In this study, a total of 15 patients had visceral metastases, including 9 patients with hepatic lesions, 7 with parenchymal lung nodules, and 2 with pleural masses. Only 2 patients presented with visceral-only disease, while the other had co-existing osseous involvement. The timeline for each patient is shown in FIG. 16 starting from the time of first CTC enumeration in this study to the end of follow-up. FIG. 16 shows a graph summarizing the 15 patients with visceral metastases. The beginning of each timeline (Day 0) indicates the time of first CTC enumeration by NanoVelcro Chips. The end of each timeline is the time of the end of follow-up. There are 3 patients (1117, 1161, 3701) initially presented with osseous/nodal metastases and later developed visceral lesions. vsnCTCs were found in these patients prior to radiographic detection of visceral metastases with the lead time ranging from 104 to 196 days (typical example see patient A in FIG. 17A). Detailed clinical history of two other example cases (patient B and C) and observations on their vsnCTCs were presented in FIG. 17B and FIG. 18.

Figures 17A, 17B:
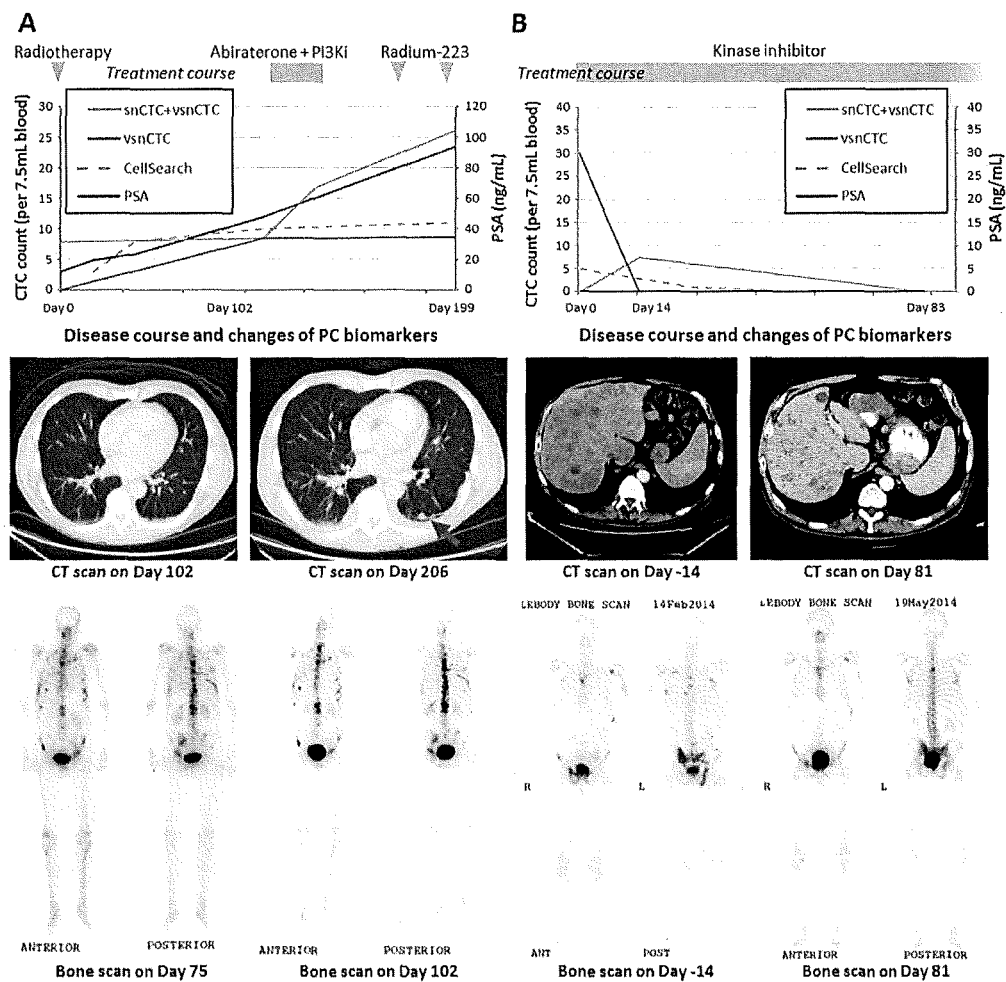
FIGS. 17A-17B show data graphs, CT scans and bone scans of individual clinical cases displaying a correlation between vsnCTC and visceral metastasis.

FIGS. 17A-17B show data graphs, CT scans and bone scans of individual clinical cases displaying a correlation between vsnCTC and visceral metastasis. Detailed clinical history of patient A was shown in (FIG. 17A) as an example of vsnCTC predicting the new visceral metastasis. Patient A presented with a locally advanced, high grade PC that relapsed and progressed to metastatic castration resistant PC (mCRPC). He was treated with a series of systemic therapies including abiraterone acetate, docetaxel, radium-223, and an experimental PI3K inhibitor. He experienced limited biochemical and clinical benefit from therapy and eventually developed a pulmonary metastasis followed by rapid clinical deterioration and death. At the outset of the serial CTC analysis, imaging by CT and bone scan confirmed that his macroscopic disease burden was limited to osseous spread. We identified the emergence of vsnCTCs, which preceded the development of the lung metastasis by approximately 100 days. These vsnCTC persisted for the remainder of his disease course. (FIG. 17B) Patient B was a mCRPC patient with known liver metastases that developed early in his natural history. His disease progressed radiographically (without rising serum PSA concentration) despite ADT and docetaxel. He began CTC collections during participation on a clinical trial with an investigational multi-targeted kinase inhibitor. The patient experienced a clinical improvement within 2 weeks of starting therapy and soft tissue and bone response was noted at 3 months. At his first draw this patient was found to have 30 CTCs/7.5 mL identified by the NanoVelcro Chip (versus 5 CTCs/7.5 mL by CellSearch™ system), all of which were vsnCTCs. Within 2 weeks of starting therapy, his CTC counts were 7.5 snCTCs/7.5 mL and 0 vsnCTCs/7.5 mL. The CTC counts have further declined and he continues to benefit therapy at the time of this publication. The changes of CTC counts in Patient B's clinical history suggested that vsnCTCs may be used to monitor clinical/radiographic response.

We successfully detected vsnCTCs using NanoVelcro Chips in all 12 patients who presented with visceral metastases. The other 3 patients had osseous/nodal metastases initially, but later developed metastatic lesions in visceral organ. vsnCTCs were found in these patients prior to radiographic detection of visceral lesions with the lead time ranging from 104 to 196 days (typical example see patient A in FIG. 17A). These patients received a variety of therapeutic interventions for their visceral disease, including platinum-based and taxane-based chemotherapies, radium-223, bicalutamide, abiraterone, enzalutamide, and an investigational multi-kinase inhibitor. There were no patients in our series that developed or presented with visceral metastases that did not have detectable vsnCTCs. At the time when this study concluded, 47% (7/15) of the patients died from their disease.

Figures 18A, 18B:
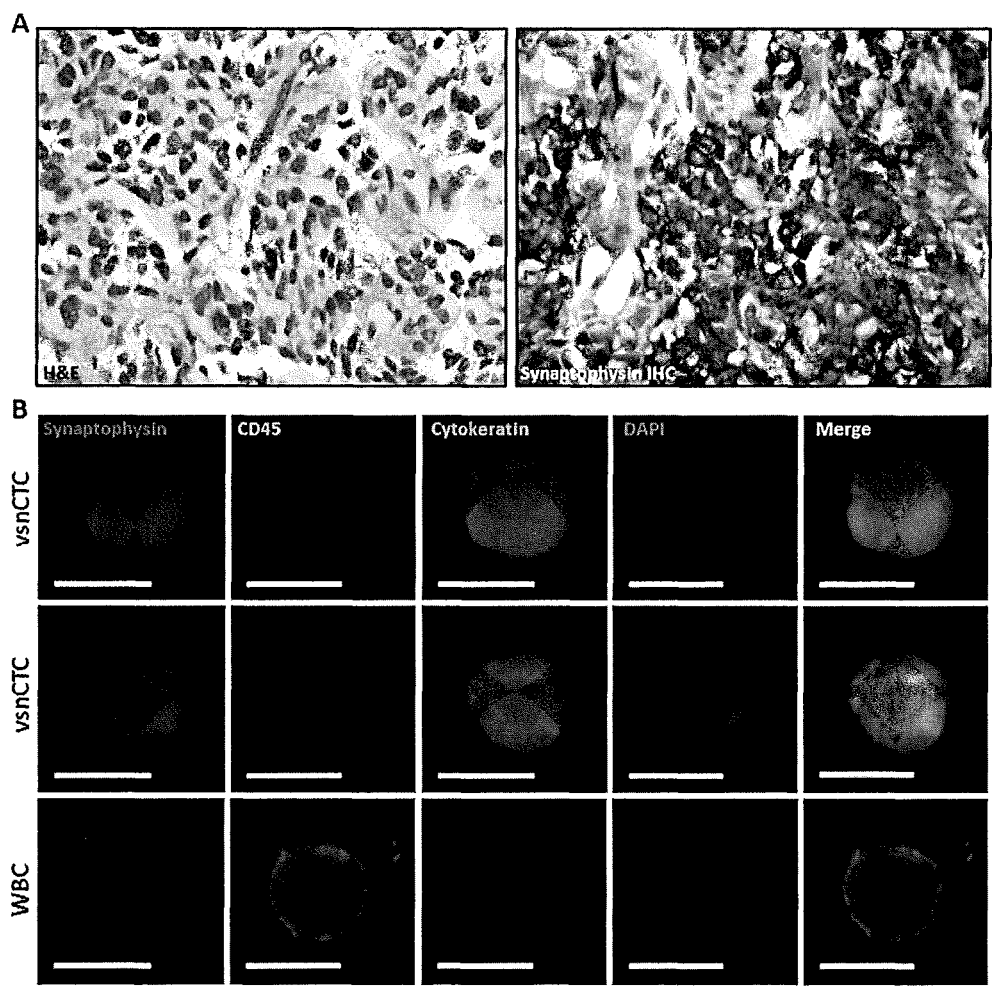
FIGS. 18A-18B show images of immunohistochemical assays demonstrating shared marker expression between vsnCTCs and metastatic tumor tissues.

FIGS. 18A-18B show images of immunohistochemical assays demonstrating shared marker expression between vsnCTCs and metastatic tumor tissues. Patient C was pathologically diagnosed with small cell carcinoma of prostate. He underwent prostatectomy followed by adjuvant radiotherapy and platinum-based chemotherapy. He relapsed radiographically 1 year later without PSA elevation and was found to have new pulmonary and osseous metastases. This patient underwent a biopsy of a pleural metastasis with a blood collection for CTC analysis. (FIG. 18A) Representative images from 4 μm-thick paraffin embedded tissue sections of a metastatic PC tumor at the pleural cavity. Tissue samples were fixed in 10% formalin. Left: a hematoxylin and eosin (H&E) stained section, original magnification 400×; right: immunohistochemical (IHC) analysis for synaptophysin expression in the pleural tumor section. (FIG. 18B) Synaptophysin staining on vsnCTCs and WBC obtained contemporarily. The scale bars in the figures indicate 10 µm.

Discussion

CTC biology has been area of rapid development in several tumor models including PC. Their value has been clearly demonstrated in enumeration.[10-17] Newer technologies have further refined our ability to analyze the pool of CTCs creating an opportunity to extract more useful clinical information from this easily obtained source of cancer cells. Our group has pioneered the use of the NanoVelcro Chip which utilizes a precisely engineered nanosubstrate and microfluidics that allows us to take advantage of cell surface marker expression (such as EpCAM) to capture CTCs from whole blood. As demonstrated in this study and in previous publications[26, 27], NanoVelcro Chips exhibited higher sensitivity in detecting live CTCs from peripheral blood (also see FIGS. 19A-19B) than currently used approach in the clinic. Moreover, by incorporating fluorescence microscopy with NanoVelcro Chips, we generated cell images amenable to formal histopathologic review.

Figures 19A, 19B:
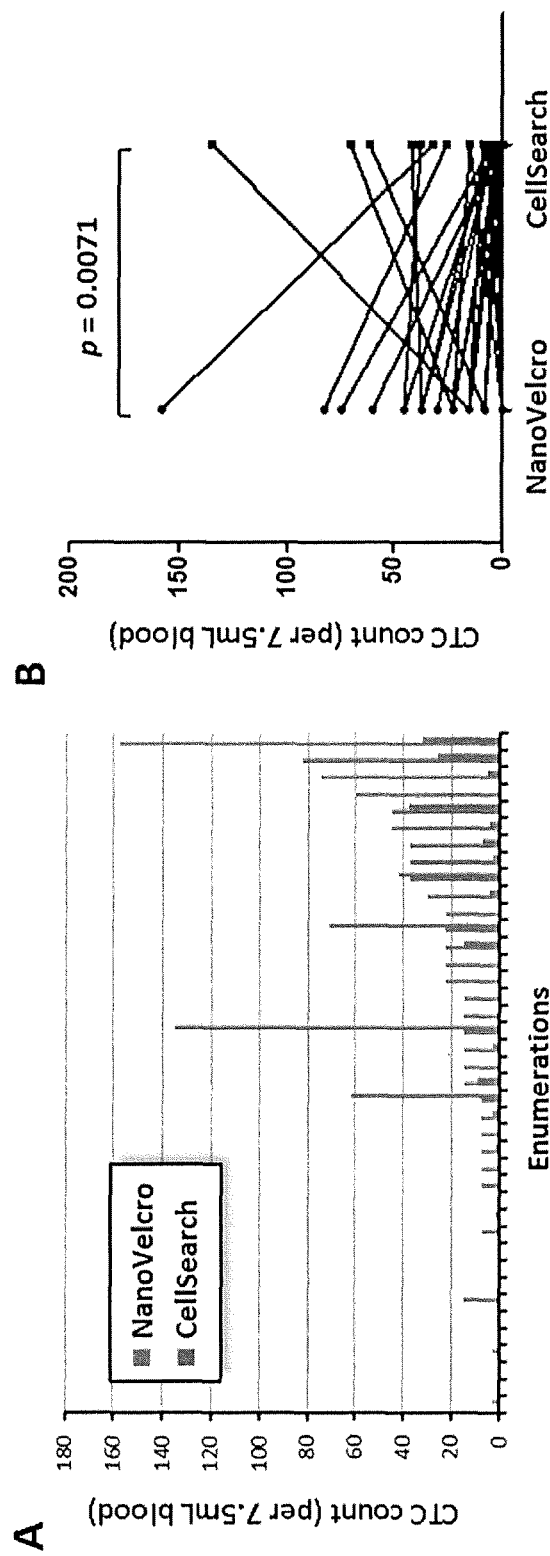
FIGS. 19A-19B show graphs demonstrating that NanoVelcro Chip has higher sensitivity for CTC identification compared to CellSearch™ system.

FIGS. 19A-19B show graphs demonstrating that NanoVelcro Chip has higher sensitivity for CTC identification compared to CellSearch™ system. In this study, we identified a total of 40 enumeration studies among the 124 ones that had CellSearch™ assay performed at the same time or within a two-week interval. Side-by-side comparison of the CTC counts of these 40 pairs of enumeration studies was plotted in (FIG. 19A). A Wilcoxon matched pairs test was performed which showed the CTC counts obtained using NanoVelcro CTC Chips (mean: 21.38 cells/7.5 mL blood; 95% confidence interval: 11.67 to 31.08) significantly higher ($p=0.0071$) than those obtained using CellSearch™ system (mean: 12.35 cells/7.5 mL blood; 95% confidence interval: 3.99 to 20.71), as demonstrated in (FIG. 19B).

Histopathology remains the gold standard for cancer diagnosis and classification. Morphological features have been linked to clinical behavior in a variety of diseases including prostate cancer (e.g. Gleason Scoring). However, this type of histopathologic review has not been typically applied to CTC isolation strategies. Here, we applied this underappreciated and fundamental concept to a highly sensitive and specific CTC enumeration approach based on the NanoVelcro Chip technology. This refined process identified a potential source of false-positive events from leukocytes and other non-epithelial cells. This same approach also enabled us to perform nuclear size measurements on individual CTCs. Among the commonly used morphologic features, we found nuclear sizes to be the most robust feature for the NanoVelcro substrate-immobilized CTCs due to: 1) the high reproducibility of DAPI staining and 2) the minimal attenuation of DAPI fluorescence during the imaging process. Moreover, we acknowledge that in our experience and the reports of other groups, the cellular membrane of CTCs is extremely fragile and susceptible to generation of artifacts and disruption by mechanical forces.[35] In contrast, the nuclear morphology was rather well-preserved during the entire CTC enumeration process. As a result, we focused on measuring the size of nuclei in this observational study and revealed three different subpopulations of CTCs using nuclear size, namely lnCTCs, snCTCs and vsnCTCs.

Our study points toward a potential benefit in adding simple morphologic categorization (i.e., nuclear size) to CTC enumeration. Most importantly, this observation lays the foundation for exploring vsnCTCs as a putative biomarker for emerging visceral metastases in PC patients. It has been reported that clinically and/or radiographically detectable visceral metastases are found in less than 20% of patients in reported case series.[3] While this is a minority of patients, it is also recognized that patients who develop visceral metastases have poorer outcomes that those patient with bone and/or lymph node only disease.[2-5] It has been argued that this clinical behavior identifies an aggressive PC subtype which has not been well studied. Patients with (or those who are at risk of) visceral metastases are an important subcategory of PC patients. Our observation could serve as the basis for a clinical test that could help to identify men at high-risk for visceral metastases and hence mortality from organ failure due to PC. As such, this approach could create an opportunity for early intervention that may impact the negative outcomes related to visceral metastases such as early cytotoxic therapy as demonstrated in E3805[36].

Our focus on patients with visceral metastases necessarily limits the sample size achievable in single institution and is a limitation of this exploratory study. It is also important to recognize that metastatic status can change over time—subsets of patients will develop visceral disease while other will have progressive bone lesions only. As such, we and others have hypothesized that the major CTC subsets in circulation may shift as this process occurs.[37] It is conceivable that one may detect different CTC subsets at different time points corresponding to different disease status, and the correlation between CTC subsets and radiographic pattern of metastatic spread could still be made using serial specimen collection and enumeration studies for each patient. Therefore, we included serial samples from patients in the correlational analysis considering each enumeration study as an independent event that reflects the current status of the patient's disease. While this raises concern over bias from repeated sampling from certain patients, the GLMMs tests performed showed that the findings of the Wilcoxon test were still valid. Our results indicated that snCTC+vsnCTC counts were significantly higher in metastatic PC compared to the no metastasis category. Furthermore, vsnCTC counts were significantly higher in aggressive PC with visceral involvement compared to the PC with only osseous and nodal metastases. The observation we report appears to hold true using two independent statistical tests.

Within our patient cohort, we observed that in patients who are undergoing serial CTC enumerations, vsnCTCs were identified prior to the radiographic detection of visceral metastatic lesions (patient A in FIG. 17A). This raises the possibility that vsnCTCs may have predictive value with respect to progression to visceral metastasis. We point out that vsnCTCs are not exclusively detected in the setting of existing/detectable) visceral metastases. However, it is possible that patients in whom vsnCTCs are detected could be at increased risk of development of visceral disease.

Like dynamic changes in CTC counts measured by CellSearch[38-40], changes in vsnCTCs counts may also reflect a positive impact from anti-cancer therapy[27, 37-39]. Each CTC subset may also exhibit variations in response to therapies. While this report is limited by the sample size and the heterogeneity in the therapeutic interventions, we have observed that visceral metastasis patients who are therapeutic responders have shown trends toward vsnCTC reduction in the face of treatment (typical example see patient B in FIG. 17B).[41] A larger prospective study is ongoing to further validate these observations with more longitudinal cases and less heterogeneity in treatment options.

Progression to visceral metastases indicates a change in the underlying molecular mechanisms[42] driving the metastatic process in PC. An example of such an alteration would be differentiation toward a more neuroendocrine phenotype of PC (NEPC).[7] We report an interesting observation in such a patient (patient C in FIGS. 18A-18B). This patient underwent a biopsy of a pleural lesion which was found to express CK and synaptophysin. On analysis of his vsnCTCs also reflected this immunophenotype. This is particularly interesting as synaptophysin is a recognized marker for NEPC[7] that has not been previously reported in PC CTCs. While this finding is limited to an isolated case report, it not only demonstrated the vsnCTC-tumor relationship in this patient but also supported the idea of including additional cellular marker in CTC enumeration for more clinical information.

In addition to the prognostic utility of CTC count, significant research endeavors have been devoted to characterizing the molecular nature of CTCs using genomic[43-45], transcriptomic[46], and proteomic approaches[47, 48], as well as exploring the functional properties of CTCs based on ex vivo expansion[49] and xenograft assays[50]. Interestingly, recent studies also re-emphasized the significance of morphologic analysis by pointing out that CTC clusters with an increased mesenchymal phenotype have increased metastatic potential[51] and correlate with poor prognosis[52], which were consistent with early observations[53] in histopathology. Our findings echo these studies by showing the importance of CTC nuclear size and its relevance to cancer stage and clinical behaviors. Considering the possible paradigm that it is the combination of variation across all possible omic levels in concert that leads to phenotype[54], our observation provides an excellent chance for future studies to comprehensively characterize this aggressive phenotype of PC at different omic levels.

In summary, we report an initial observation that CTC subsets defined by nuclear sizes may have clinical relevance. The NanoVelcro assay we utilized provided a high degree of sensitivity and specificity for CTC identification while making nuclear size assessment possible. While we recognized that this innovative finding has been made in a small patient cohort, the emergence of the CTC subsets and their relationship to clinical metastatic status appeared surprisingly robust. Larger-scale, prospective trials should be conducted to validate this initial observation and investigate its potential application in the detection and perhaps prediction of visceral metastasis. This observation also points towards the importance of understanding the biochemical nature of the vsnCTC to further delineating their relevance in metastatic PC. Given the fundamental nature of morphologic analysis in pathology, we propose that morphologic characterization be incorporated into CTC enumerations and that further studies of the vsnCTCs be conducted to explore its relationship to visceral metastasis.

References for Example 2

1. Siegel R, Ma J, Zou Z, Jemal A. Cancer statistics, 2014. *CA Cancer J Clin.* 2014; 64: 9-29.
2. Pezaro C J, Omlin A, Lorente D, et al. Visceral disease in castration-resistant prostate cancer. *Eur Urol.* 2014; 65: 270-273.
3. Gandaglia G, Karakiewicz P I, Briganti A, et al. Impact of the Site of Metastases on Survival in Patients with Metastatic Prostate Cancer. *Eur Urol.* 2014.
4. Pond G R, Sonpavde G, de Wit R, Eisenberger M A, Tannock I F, Armstrong A J. The prognostic importance of metastatic site in men with metastatic castration-resistant prostate cancer. *Eur Urol.* 2014; 65: 3-6.
5. Halabi S, Kelly W K, Zhou H, et al. The site of visceral metastases (mets) to predict overall survival (OS) in castration-resistant prostate cancer (CRPC) patients (pts): A meta-analysis of five phase III trials. *J Clin Oncol.* 2014: 5s, 2014 (suppl; abstr 5002).
6. Vinjamoori A H, Jagannathan J P, Shinagare A B, et al. Atypical metastases from prostate cancer: 10-year experience at a single institution. *AJR Am J Roentgenol.* 2012; 199: 367-372.
7. Beltran H, Tomlins S, Aparicio A, et al. Aggressive Variants of Castration-Resistant Prostate Cancer. *Clin Cancer Res.* 2014.
8. Beltran H, Tagawa S T, Park K, et al. Challenges in recognizing treatment-related neuroendocrine prostate cancer. *J Clin Oncol.* 2012; 30: e386-389.
9. Danila D C, Fleisher M, Scher H I. Circulating tumor cells as biomarkers in prostate cancer. *Clin Cancer Res.* 2011; 17: 3903-3912.
10. Goldkorn A, Ely B, Quinn D I, et al. Circulating tumor cell counts are prognostic of overall survival in SWOG S0421: a phase III trial of docetaxel with or without atrasentan for metastatic castration-resistant prostate cancer. *J Clin Oncol.* 2014; 32: 1136-1142.
11. Resel Folkersma L, San Jose Manso L, Galante Romo I, Moreno Sierra J, Olivier Gomez C. Prognostic significance of circulating tumor cell count in patients with metastatic hormone-sensitive prostate cancer. *Urology.* 2012; 80: 1328-1332.
12. Wang F B, Yang X Q, Yang S, Wang B C, Feng M H, Tu J C. A higher number of circulating tumor cells (CTC) in peripheral blood indicates poor prognosis in prostate cancer patients—a meta-analysis. *Asian Pac J Cancer Prev.* 2011; 12: 2629-2635.
13. Scher H I, Jia X, de Bono J S, et al. Circulating tumour cells as prognostic markers in progressive, castration-resistant prostate cancer: a reanalysis of IMMC38 trial data. *Lancet Oncol.* 2009; 10: 233-239.
14. Olmos D, Arkenau H T, Ang J E, et al. Circulating tumour cell (CTC) counts as intermediate end points in castration-resistant prostate cancer (CRPC): a single-centre experience. *Ann Oncol.* 2009; 20: 27-33.
15. de Bono J S, Scher H I, Montgomery R B, et al. Circulating tumor cells predict survival benefit from treatment in metastatic castration-resistant prostate cancer. *Clin Cancer Res.* 2008; 14: 6302-6309.
16. Moreno J G, Miller M C, Gross S, Allard W J, Gomella L G, Terstappen L W. Circulating tumor cells predict survival in patients with metastatic prostate cancer. *Urology.* 2005; 65: 713-718.
17. Thalgott M, Rack B, Maurer T, et al. Detection of circulating tumor cells in different stages of prostate cancer. *J Cancer Res Clin Oncol.* 2013; 139: 755-763.
18. Wicha M S, Hayes D F. Circulating tumor cells: not all detected cells are bad and not all bad cells are detected. *J Clin Oncol.* 2011; 29: 1508-1511.
19. Alix-Panabieres C, Pantel K. Challenges in circulating tumour cell research. *Nat Rev Cancer.* 2014; 14: 623-631.
20. Ligthart S T, Coumans F A, Bidard F C, et al. Circulating Tumor Cells Count and Morphological Features in Breast, Colorectal and Prostate Cancer. *PLoS One.* 2013; 8: e67148.
21. Marrinucci D, Bethel K, Bruce R H, et al. Case study of the morphologic variation of circulating tumor cells. *Hum Pathol.* 2007; 38: 514-519.

22. Bobek V, Hoffman R M, Kolostova K. Site-specific cytomorphology of disseminated PC-3 prostate cancer cells visualized in vivo with fluorescent proteins. *Diagn Cytopathol*. 2013; 41: 413-417.
23. Partin A W, Steinberg G D, Pitcock R V, et al. Use of nuclear morphometry, gleason histologic scoring, clinical stage, and age to predict disease-free survival among patients with prostate cancer. *Cancer*. 1992; 70: 161-168.
24. Mohler J L, Figlesthaler W M, Zhang X Z, Partin A W, Maygarden S J. Nuclear shape analysis for the assessment of local invasion and metastases in clinically localized prostate carcinoma. *Cancer*. 1994; 74: 2996-3001.
25. Khan M A, Walsh P C, Miller M C, et al. Quantitative alterations in nuclear structure predict prostate carcinoma distant metastasis and death in men with biochemical recurrence after radical prostatectomy. *Cancer*. 2003; 98: 2583-2591.
26. Zink D, Fischer A H, Nickerson J A. Nuclear structure in cancer cells. *Nat Rev Cancer*. 2004; 4: 677-687.
27. Wang S, Liu K, Liu J, et al. Highly efficient capture of circulating tumor cells by using nanostructured silicon substrates with integrated chaotic micromixers. *Angew Chem Int Ed Engl*. 2011; 50: 3084-3088.
28. Lu Y T, Zhao L, Shen Q, et al. NanoVelcro Chip for CTC enumeration in prostate cancer patients. *Methods*. 2013 64: 144-152.
29. Vesalainen S, Lipponen P, Talja M, Kasurinen J, Syrjanen K. Nuclear morphometry is of independent prognostic value only in T1 prostatic adenocarcinomas. *Prostate*. 1995; 27: 110-117.
30. Klingauf M, Stanek D, Neugebauer K M. Enhancement of U4/U6 small nuclear ribonucleoprotein particle association in Cajal bodies predicted by mathematical modeling. *Mol Biol Cell*. 2006; 17: 4972-4981.
31. Dempster A P, Laird N M, Rubin D B. Maximum Likelihood from Incomplete Data via the EM Algorithm *Journal of the Royal Statistical Society, Series B*. 1977; 39: 1-38.
32. Akaike H. A new look at the statistical model identification. *IEEE Transactions Automatic Control*. 1974; 19: 716-723.
33. Schwarz G E. Estimating the dimension of a model. *Annals of Statistics*. 1978; 6: 461-464.
34. Broström G. Generalized linear models with clustering 2009. Available from URL: http://cran.r-project.org/web/packages/glmmML/glmmML.pdf.
35. Lin M, Chen J F, Lu Y T, et al. Nanostructure embedded microchips for detection, isolation, and characterization of circulating tumor cells. *Acc Chem Res*. 2014; 47: 2941-2950.
36. Sweeney C, Chen Y-H, Carducci M A, et al. Impact on overall survival (OS) with chemohormonal therapy versus hormonal therapy for hormone-sensitive newly metastatic prostate cancer (mPrCa): An ECOG-led phase III randomized trial. *J Clin Oncol*. 2014: 5s, 2014 (suppl; abstr LBA2012).
37. Krebs M G, Metcalf R L, Carter L, Brady G, Blackhall F H, Dive C. Molecular analysis of circulating tumour cells-biology and biomarkers. *Nat Rev Clin Oncol*. 2014; 11: 129-144.
38. Attard G, Reid A H, A'Hern R, et al. Selective inhibition of CYP17 with abiraterone acetate is highly active in the treatment of castration-resistant prostate cancer. *J Clin Oncol*. 2009; 27: 3742-3748.
39. Reid A H, Attard G, Danila D C, et al. Significant and sustained antitumor activity in post-docetaxel, castration-resistant prostate cancer with the CYP17 inhibitor abiraterone acetate. *J Clin Oncol*. 2010; 28: 1489-1495.
40. Danila D C, Morris M J, de Bono J S, et al. Phase II multicenter study of abiraterone acetate plus prednisone therapy in patients with docetaxel-treated castration-resistant prostate cancer. *J Clin Oncol*. 2010; 28: 1496-1501.
41. Posadas E M, Tighiouart M, Chen J-F, et al. A translational phase 2 study of cabozantinib in men with metastatic castration resistant prostate cancer with visceral metastases with characterization of circulating tumor cells and large oncosomes. *Annals of Oncology*. 2014; 25 (suppl_4): iv546-iv563.
42. Akfirat C, Zhang X, Ventura A, et al. Tumour cell survival mechanisms in lethal metastatic prostate cancer differ between bone and soft tissue metastases. *J Pathol*. 2013; 230: 291-297.
43. Zhao L, Lu Y T, Li F, et al. High-Purity Prostate Circulating Tumor Cell Isolation by a Polymer Nanofiber-Embedded Microchip for Whole Exome Sequencing. *Adv Mater*. 2013.
44. Hou S, Zhao L, Shen Q, et al. Polymer nanofiber-embedded microchips for detection, isolation, and molecular analysis of single circulating melanoma cells. *Angew Chem Int Ed Engl*. 2013; 52: 3379-3383.
45. Lohr J G, Adalsteinsson V A, Cibulskis K, et al. Whole-exome sequencing of circulating tumor cells provides a window into metastatic prostate cancer. *Nat Biotechnol*. 2014; 32: 479-484.
46. Yu M, Bardia A, Wittner B S, et al. Circulating breast tumor cells exhibit dynamic changes in epithelial and mesenchymal composition. *Science*. 2013; 339: 580-584.
47. Chan C M, Au T C, Chan A T, et al. Advanced technologies for studying circulating tumor cells at the protein level. *Expert Rev Proteomics*. 2013; 10: 579-589.
48. Scatena R, Bottoni P, Giardina B. Circulating tumour cells and cancer stem cells: a role for proteomics in defining the interrelationships between function, phenotype and differentiation with potential clinical applications. *Biochim Biophys Acta*. 2013; 1835: 129-143.
49. Yu M, Bardia A, Aceto N, et al. Cancer therapy. Ex vivo culture of circulating breast tumor cells for individualized testing of drug susceptibility. *Science*. 2014; 345: 216-220.
50. Baccelli I, Schneeweiss A, Riethdorf S, et al. Identification of a population of blood circulating tumor cells from breast cancer patients that initiates metastasis in a xenograft assay. *Nat Biotechnol*. 2013; 31: 539-544.
51. Aceto N, Bardia A, Miyamoto D T, et al. Circulating tumor cell clusters are oligoclonal precursors of breast cancer metastasis. *Cell*. 2014; 158: 1110-1122.
52. Hou J M, Krebs M G, Lancashire L, et al. Clinical significance and molecular characteristics of circulating tumor cells and circulating tumor microemboli in patients with small-cell lung cancer. *J Clin Oncol*. 2012; 30: 525-532.
53. Liotta L A, Saidel M G, Kleinerman J. The significance of hematogenous tumor cell clumps in the metastatic process. *Cancer Res*. 1976; 36: 889-894.
54. Ritchie M D, Holzinger E R, Li R, Pendergrass S A, Kim D. Methods of integrating data to uncover genotype-phenotype interactions. *Nat Rev Genet*. 2015; 16: 85-97.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of assessing a disease condition of a cancer of a subject, comprising:
   receiving a blood sample from said subject;
   isolating a plurality of circulating tumor cells (CTCs) from said blood sample;
   measuring at least one of cell or cell nucleus sizes of each of said plurality of CTCs;
   determining a measured CTC size distribution of said plurality of CTCs based on said measuring;
   comparing said measured CTC size distribution to a reference CTC size distribution using a computer; and
   assigning said disease condition of said cancer of said subject based on said comparing.

2. The method of claim 1, wherein said assigning is an automated assigning performed by said computer.

3. The method of claim 1, wherein said isolating said plurality of CTCs is performed using a device that has a nanostructured surface that enhances capture of CTCs preferentially over other types of cells.

4. The method of claim 1, wherein said reference distribution is an empirically obtained size distribution that is resolved into a plurality of size-cluster distributions.

5. The method of claim 4, wherein said plurality of size-cluster distributions is three different size-cluster distributions corresponding to large-nuclear CTCs, small-nuclear CTCs and very-small-nuclear CTCs, respectively.

6. The method of claim 1, wherein said assigning said disease condition of said cancer comprises assigning a metastatic stage of said cancer.

7. The method of claim 6, wherein said assigning said metastatic stage of said cancer comprises assigning a visceral metastatic stage based at least on a component of very-small-nuclear CTCs in said measured CTC size distribution.

8. The method of claim 1, wherein said receiving said blood sample is receiving a whole-blood sample.

9. The method of claim 1, wherein said measuring at least one of cell or cell nucleus sizes measures a longest dimension of said each of said CTCs, measures a dimension perpendicular to each corresponding longest axis, takes a product of each longest dimension and corresponding perpendicular dimensions, and takes the square root of each said product.

10. The method of claim 1, wherein said disease condition of said cancer is at least one of a presence of metastasis, a location of metastasis or a disease stage of said cancer.

11. The method of claim 1, further comprising subjecting said blood sample to red blood cell depletion prior to said isolating of said plurality of circulating tumor cells (CTCs) from said blood sample.

12. The method of claim 3, wherein said device also has a microfluidic chaotic mixer that contributes to further enhancing capture of CTCs preferentially over other types of cells.

13. The method of claim 12, wherein said nanostructured surface is coated with streptavidin.

14. The method of claim 1, further comprising incubating said blood sample with a capture agent prior to said isolating said plurality of circulating tumor cells (CTCs) from said blood sample.

15. The method of claim 14, wherein said capture agent is a biotinylated antibody.

16. The method of claim 1, wherein said isolating said plurality of CTCs further comprises immobilizing said plurality of CTCs and subjecting said plurality of CTCs to immunohistochemistry.

17. The method of claim 1, wherein the cancer is prostate cancer.

18. The method of claim 3, wherein said isolating said plurality of CTCs comprises capturing said CTCs on said nanostructured surface such that said plurality of CTCs remain living, viable CTCs.

19. A method of assigning a metastatic stage of prostate cancer, comprising:
    receiving a blood sample from a subject with prostate cancer;
    isolating a plurality of circulating tumor cells (CTCs) from said blood sample using a device that has a nanostructured surface that enhances capture of CTCs preferentially over other types of cells and uses a combination of a microfluidic chaotic mixer and said nanostructured surface;
    measuring at least one of cell or cell nucleus sizes of each of said plurality of CTCs;
    determining a measured CTC size distribution of said plurality of CTCs based on said measuring;
    comparing said measured CTC size distribution to a reference CTC size distribution using a computer; and
    assigning a metastatic stage of said prostate cancer of said subject based on said comparing.

20. The method of claim 19, wherein said reference distribution is an empirically obtained size distribution that is resolved into a plurality of size-cluster distributions, wherein said plurality of size-cluster distributions is three different size-cluster distributions corresponding to large-nuclear CTCs, small-nuclear CTCs and very-small-nuclear CTCs, respectively.

21. The method of claim 19, wherein said assigning said metastatic stage of said cancer comprises assigning a visceral metastatic stage based at least on a component of very-small-nuclear CTCs in said measured CTC size distribution.

22. The method of claim 19, wherein said measuring at least one of cell or cell nucleus sizes measures a longest dimension of said each of said CTCs, measures a dimension perpendicular to each corresponding longest axis, takes a product of each longest dimension and corresponding perpendicular dimensions, and takes the square root of each said product.

23. The method of claim 19 further comprising using immunohistochemistry to detect expression of a biomarker specific for prostate cancer in the isolated plurality of circulating tumor cells (CTCs).

* * * * *